United States Patent [19]
Ramsdell et al.

[11] Patent Number: 5,717,735
[45] Date of Patent: Feb. 10, 1998

[54] MEDICAL RADIOLOGICAL APPARATUS INCLUDING OPTICAL CROSSHAIR DEVICE FOR PATIENT POSITIONING AND FOREARM AND SPINAL POSITIONING AIDES

[75] Inventors: Tracy L. Ramsdell, Amherst, N.H.; Tina LeFabvre, Woonsocket, R.I.

[73] Assignee: Hologic, Inc., Waltham, Mass.

[21] Appl. No.: 686,109

[22] Filed: Jul. 24, 1996

Related U.S. Application Data

[62] Division of Ser. No. 475,404, Jun. 7, 1995, which is a continuation of Ser. No. 345,069, Nov. 25, 1994, which is a continuation-in-part of Ser. No. 156,287, Nov. 22, 1993, Pat. No. 5,432,834.

[51] Int. Cl.$^6$ ...................................................... H05G 1/00
[52] U.S. Cl. ............................ 378/208; 378/195; 378/209
[58] Field of Search .................................... 378/208, 209, 378/20, 68, 195

[56] References Cited

U.S. PATENT DOCUMENTS

| | | |
|---|---|---|
| 3,803,417 | 4/1974 | Kok . |
| 3,859,982 | 1/1975 | Dove ................................. 378/208 X |
| 3,944,830 | 3/1976 | Dissing . |
| 3,988,585 | 10/1976 | O'Neill et al. . |
| 4,144,457 | 3/1979 | Albert . |
| 4,358,856 | 11/1982 | Stivender et al. . |
| 4,365,343 | 12/1982 | Grady et al. . |
| 4,400,820 | 8/1983 | O'Dell et al. ............................ 378/209 |
| 4,616,814 | 10/1986 | Harwood-Nash et al. .......... 378/208 X |
| 4,649,560 | 3/1987 | Grady et al. . |
| 4,715,057 | 12/1987 | Hahn et al. . |
| 4,716,581 | 12/1987 | Barud . |
| 4,788,429 | 11/1988 | Wilson . |
| 4,811,373 | 3/1989 | Stein . |
| 4,829,549 | 5/1989 | Vogel et al. . |
| 4,841,965 | 6/1989 | Jacobs ................................. 378/208 X |
| 4,903,203 | 2/1990 | Yamashita et al. . |

(List continued on next page.)

FOREIGN PATENT DOCUMENTS

| | | |
|---|---|---|
| 0432730 | 6/1991 | European Pat. Off. . |
| 0461028 | 12/1991 | European Pat. Off. . |
| 2238706 | 2/1974 | Germany . |
| WO8607531 | 12/1986 | WIPO . |
| WO9421174 | 9/1994 | WIPO . |

OTHER PUBLICATIONS

Lunar, A Quantum Leap in Bone Densitometry, Expert, The World's First Imaging Densitometer (undated but beleived to have been published before Nov. 22, 1992).

Lunar News, Dec. 1992, "Lunar Introduces Expert, the World's First Imaging Densitometer."

(List continued on next page.)

*Primary Examiner*—David P. Porta
*Attorney, Agent, or Firm*—Cooper & Dunham LLP

[57] ABSTRACT

A medical radiological apparatus, such as an x-ray bone densitometry apparatus includes patient positioning aides for accurate patient placement and consistent positioning during a single scanning procedure, or during subsequent procedures. An optical crosshair device helps align the patient's spine along the Y-axis of the apparatus and the patient's hips along the X-axis of the apparatus, perpendicular to the spine. Spinal and forearm positioning aides help the patient maintain consistent, comfortable positions within scans. They also enable reproducibility of patient position in subsequent scans, so that scan results from one scan to another may be compared by a medical practitioner, with reasonable assurance that the respective scan results are not unduly compromised by inconsistent patient placement. The forearm positioning aide consistently places the forearm flat on the patient support table in a proper position parallel to the longitudinal table axis. The spinal positioning aide has diverging support wings which enable the patient to maintain elbows in a position off the table, in a manner which is not likely to cause spinal movement due to arm fatigue.

5 Claims, 18 Drawing Sheets

U.S. PATENT DOCUMENTS

| | | | |
|---|---|---|---|
| 4,905,267 | 2/1990 | Miller et al. | 378/209 X |
| 5,001,739 | 3/1991 | Fischer | 378/209 |
| 5,040,199 | 8/1991 | Stein . | |
| 5,081,665 | 1/1992 | Kostich | 378/20 X |
| 5,132,995 | 7/1992 | Stein . | |
| 5,148,455 | 9/1992 | Stein . | |
| 5,155,756 | 10/1992 | Pare et al. . | |
| 5,165,410 | 11/1992 | Warne et al. . | |
| 5,172,695 | 12/1992 | Cann et al. . | |
| 5,177,776 | 1/1993 | Ohmori et al. . | |
| 5,228,068 | 7/1993 | Mazess . | |
| 5,233,713 | 8/1993 | Murphy et al. | 378/209 X |
| 5,287,546 | 2/1994 | Tesic et al. . | |
| 5,291,537 | 3/1994 | Mazess . | |
| 5,305,368 | 4/1994 | Bisek et al. . | |
| 5,306,306 | 4/1994 | Bisek et al. . | |
| 5,370,117 | 12/1994 | McLaurin, Jr. | 378/20 X |
| 5,432,834 | 7/1995 | Gershman . | |

OTHER PUBLICATIONS

Product Information, Expert, Today's Breakthrough—Tomorrow's Standard (undated, but believed to have been published before Nov. 22, 1993).

Hanson, L., et al., "Preliminary Evaluation of a New Imaging Bone Densitometer," Presented at the Fourth International Symposium on Osteoporosis, 27–31 Mar., 1993, Hong Kong.

Performance Comparison: Multiple vs. Single Beam X–ray Bone Densitometry, Hologic, Inc. Sep. 1992.

Lunar DP3 User's Manual, Dual–Photon Scanner, pp. 4, 8, 10 and 22 (undated).

Nucletron, A New Dimension In Dual–Photon Absorptiometry, Brochure, Novo Diagnostic (undated).

The Norland Model 2600 Dichromatic Bone Densitometer Brochure, Norland Corp. (undated).

"DPA gaining strength in bone scanning debate", Diagnostic Imaging, Jun. 1986, pp.102–108.

Osteotek Brochure, models 200 and 300, Medical & Scientific Enterprises, Inc. (undated).

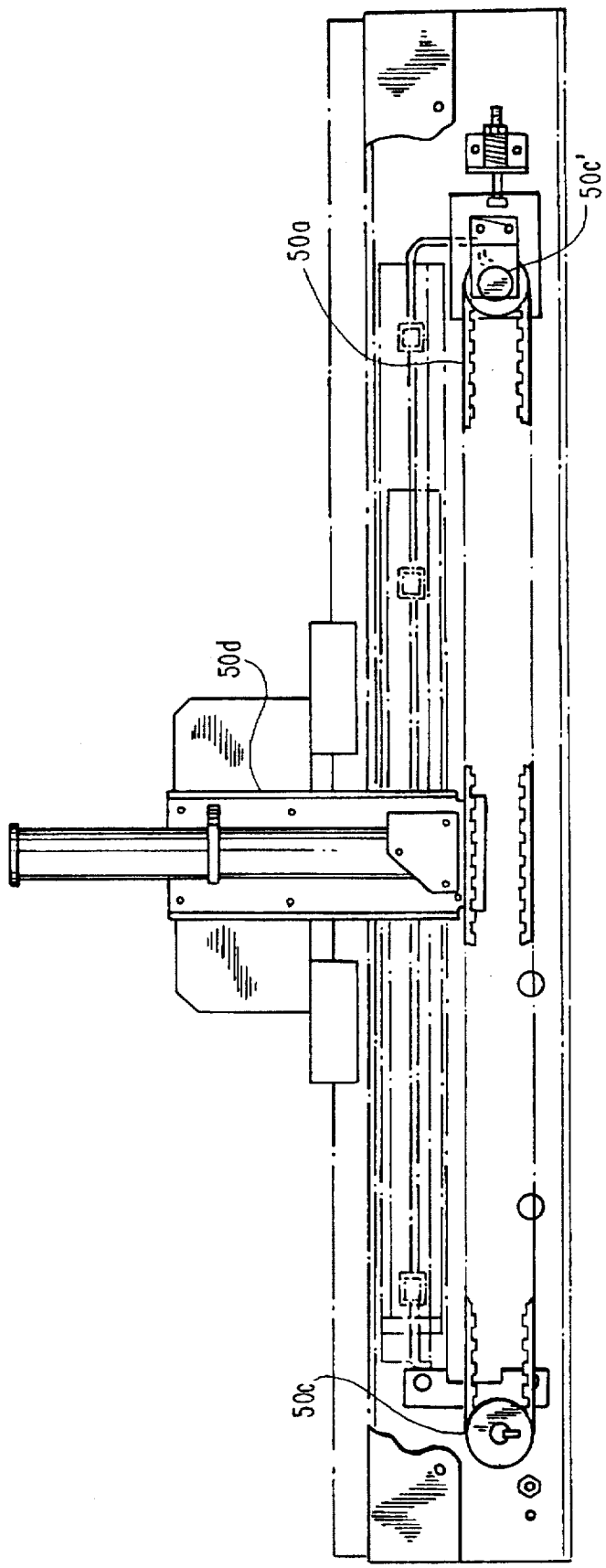

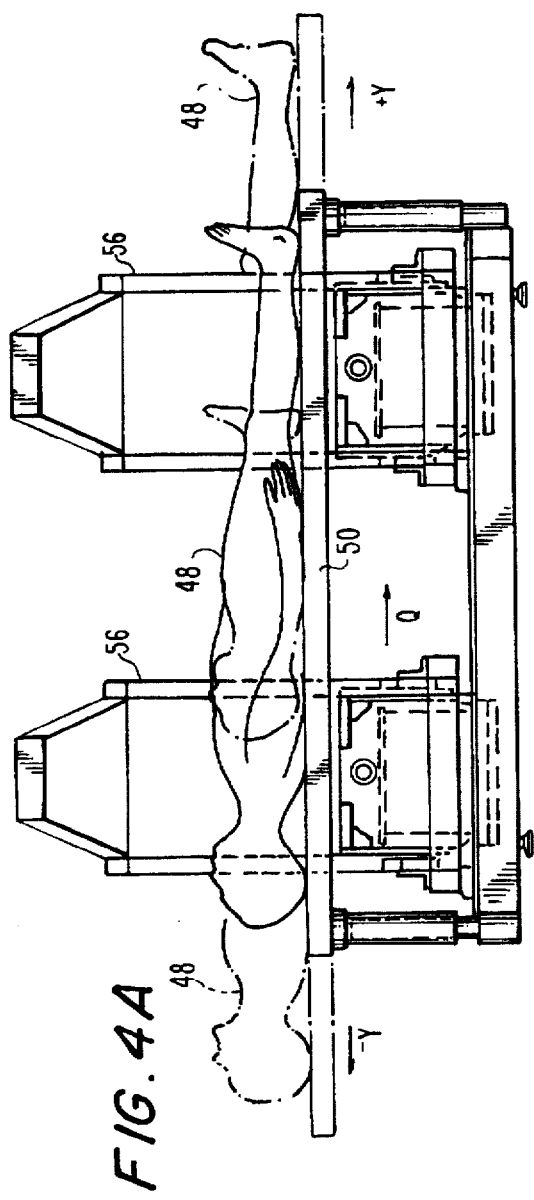
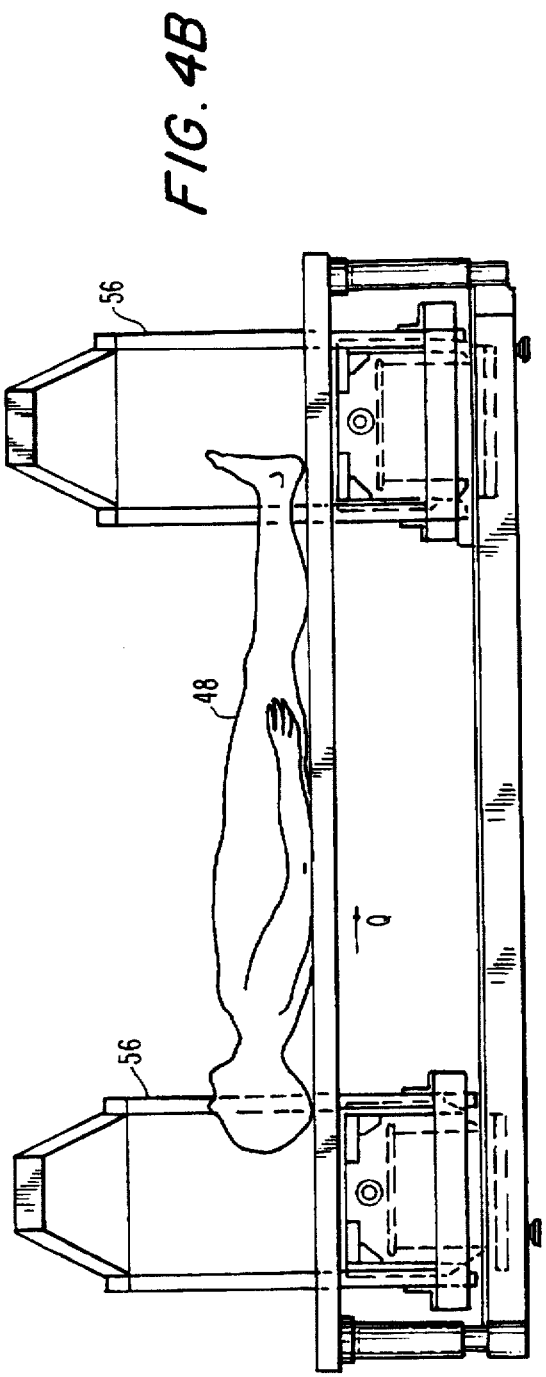

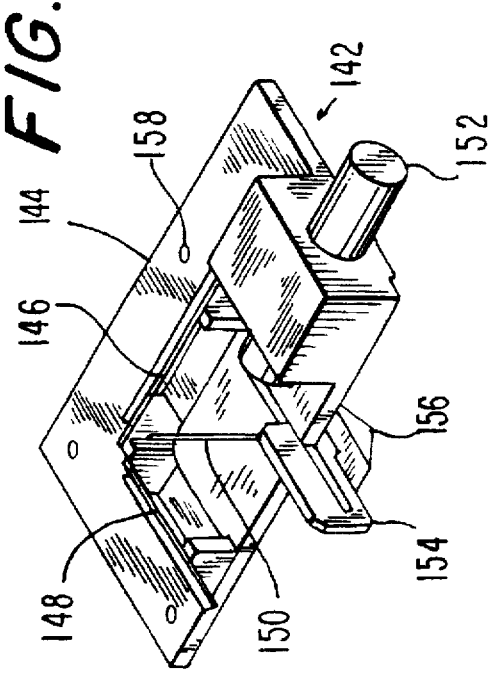
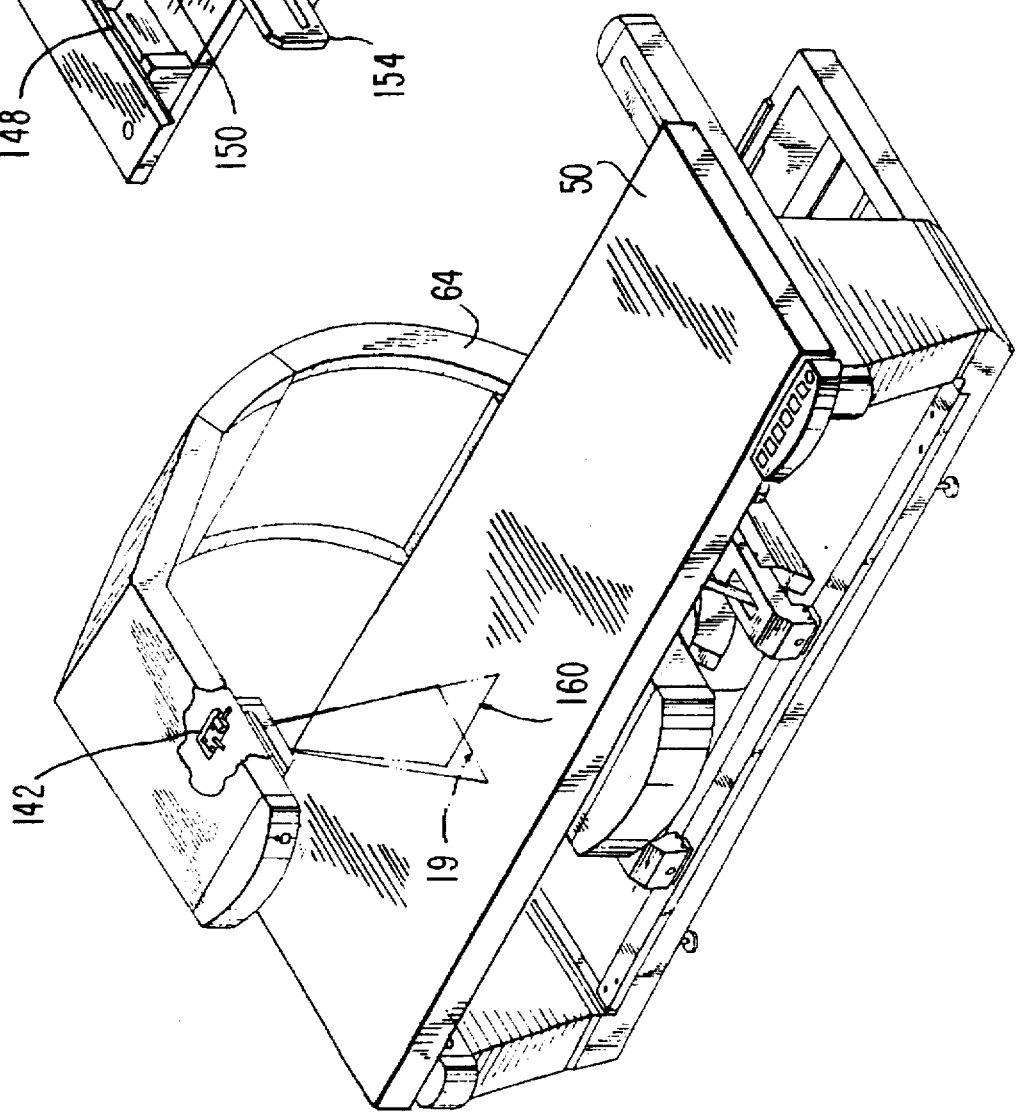

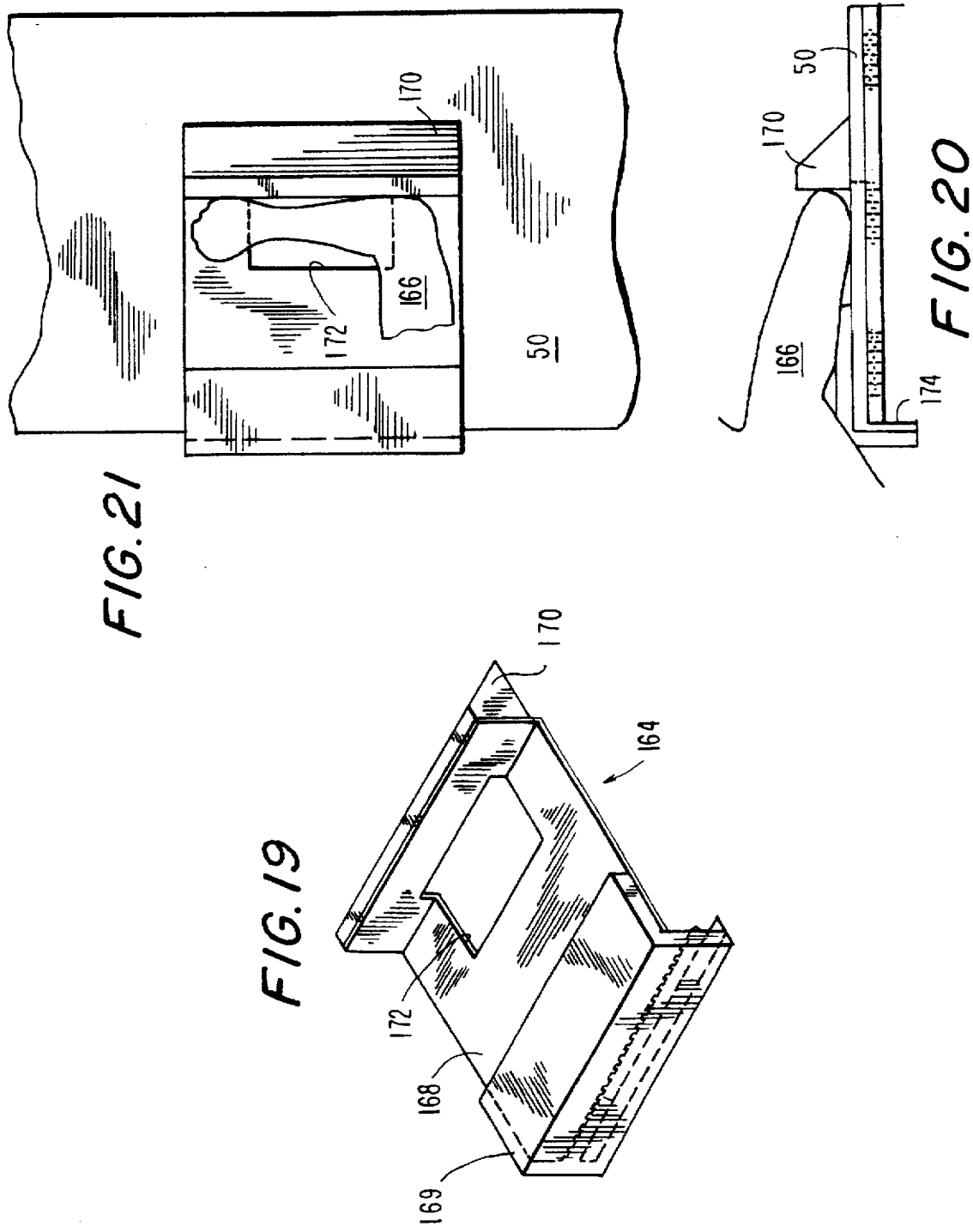

MEDICAL RADIOLOGICAL APPARATUS INCLUDING OPTICAL CROSSHAIR DEVICE FOR PATIENT POSITIONING AND FOREARM AND SPINAL POSITIONING AIDES

This is a division of application Ser. No. 08/475,404, filed Jun. 7, 1995, which is a continuation of parent application Ser. No. 08/345,069, filed on Nov. 25, 1994, which in turn is a continuation-in-part of application Ser. No. 08/156,287, filed on Nov. 22, 1993, now U.S. Pat. No. 5,432,834, both of which are hereby incorporated by reference herein as though fully set forth herein.

BACKGROUND AND SUMMARY OF THE INVENTION

The invention relates to x-ray systems and methods and more particularly to x-ray based bone densitometry systems and methods and techniques useful at least in such systems and methods.

X-rays or gamma-rays can be used to measure the density and distribution of bone in the human body in order to help health professionals assess and evaluate projected bone mineral density, which in turn can be used to monitor age-related bone loss that can be associated with diseases such as osteoporosis. Additionally or alternatively, similar procedures can be used to measure non-bone related body content such as body fat and muscle. In bone densitometry, a patient typically is placed on a table such that the patient's spine extends along the length of the table, along a direction that can be called the Y-axis in Cartesian coordinates. For a supine patient, the left and right sides are in a direction typically called the X-axis. A source at one side of the patient transmits radiation through the patient to a radiation detector at the other side. The source and the detector typically are mechanically linked by a structure such as a C-arm to ensure their alignment along a source-detector axis which is transverse (typically perpendicular) to the Y-axis. Both x-ray tubes and isotopes have been used as a source of the radiation. In each case, the radiation from the source is collimated to a specific beam shape prior to reaching the patient to thereby restrict the field of x-ray or gamma radiation to the predetermined region of the patient opposite which are located the detectors. In the case of using x-rays, various beam shapes have been used in practice including fan beam, pencil beam and cone or pyramid beam shapes. When a fan beam is used, typically the beam conforms to a beam plane which is transverse (e.g., normal) to the Y-axis. Stated differently, the beam is wide in the plane and thin along the Y-axis. The shape of the beam and the shape of the detector system correspond. The detector in a fan beam system typically is an elongated array of detector elements arranged along a line or an arc. By means of mechanically moving the C-arm and/or moving the table, a region of intrust, in a patient on the table can be scanned with the radiation. Typical regions of analysis in bone densitometry include the spine, hip, forearm, and wrist, scanned individually. They can be covered individually within a reasonable time by a fan beam that has a relatively narrow angle in a single pass or, alternatively, by a pencil beam scanning a raster pattern. Another analysis region is termed "oblique hip" in which the hip is viewed at an angle relative to the horizontal and vertical directions. Another analysis region is referred to as "whole body" in which the entire patient body is scanned and analyzed for bone density and possibly also for "body composition" or the percentages of fat and muscle in the body.

X-ray bone densitometry systems have been made by the owner of this application under the tradenames QDR-2000+, QDR-2000, QDR-1500, QDR-1000-plus, and QDR-1000. The following commonly owned U.S. Pat. pertain to such systems and are hereby incorporated by reference herein: Nos. 4,811,373, 4,947,414, 4,953,189, 5,040,199, 5,044,002; 5,054,048, 5,067,144, 5,070,519, 5,132,995 and 5,148,455; and 4,986,273 and 5,165,410 (each assigned on its face to Medical & Scientific Enterprises, Inc. but now commonly owned). Other bone densitometry systems are believed to have been made by the Lunar Corporation of Madison, Wis. (see, e.g., the system which is believed to be offered under the tradename Expert and U.S. Pat. Nos. 5,228,068, 5,287,546 and 5,305,368, none of which is admitted to be prior art against this invention). It is believed that other manufacturers also have offered bone densitometry products.

The inventions disclosed in this application are directed toward bone densitometry features which are believed to overcome various shortcomings of such prior art systems. In a particular exemplary and non-limiting embodiment, the inventions are included in an x-ray bone densitometry system comprising a patient table having a length extending along a Y-axis and a width extending along an X-axis, a C-arm supporting an x-ray source at one side and an x-ray detetector at an opposite side of said table, the source and detector being aligned along a source-detector axis which is transverse to the Y-axis. When selectively energized, the source emits a fan beam of x-rays which conforms to a beam plane which is transverse to the Y-axis and contains the source-detector axis. At least one of said C-arm and table is selectively movable relative to the other along the X-axis, along the Y-axis, and along a Z-axis which is transverse to both the X-axis and the Y-axis, to selectively scan selected regions of a patient on the table with said fan beam of x-rays. In addition, the C-arm is selectively rotatable around a rotational axis extending along the Y-axis to selectively change the angle of the fan beam with respect to a patient on the table. A beam modulator is mounted between the x-ray source and the table for rotation about a beam modulator axis which is transverse to the source-detector axis. The beam modulator is selectively rotatable about the beam modulator axis to cause the fan beam of x-rays to pass through a succession of beam modulating materials before reaching a patient on the table. These beam modulating materials having respective different effects on the x-rays impinging thereon, to modulate the beam for desired patient procedures and to serve other purposes such as to provide reference and calibration information. An attenuator selector also is mounted between the x-ray source and the table and has a plurality of attenuating materials selectively movable to cause the fan beam to pass therethrough. Each of these attenuating materials attenuates the fan beam passing therethrough in a selected manner different from that of other attenuating materials to cause a desired change in beam parameters such as intensity, uniformity and energy spectrum. A variable aperture collimator also is mounted between the x-ray source and the table to define the cross-section of the fan beam. The collimator can define the shape and size of the fan beam by passing x-rays through a selected one of several different slits in an x-ray opaque plate or, alternatively, can use a pair of plates selectively movable along the Y-axis to define one of the cross-sectional dimensions of the fan beam and a pair of plates movable along a direction transverse to both the Y-axis and the source-detector axis to define another cross-sectional dimension of the fan beam. A number of detector elements can be used to form said detector and to provide respective detector outputs related to the x-rays received at respective angular positions within the fan beam. A detector response flattener can be used which is responsive to the detector outputs to process the outputs to account for at least one of: (i) non-uniformities in the fan beam; and (ii) non-uniformities in the response of detector elements. A dark current system can be used for interleaving the detector outputs with dark current responses of the detector elements on a substantially continuous basis, so as to use a dark current corrector which is responsive to the detector outputs and the dark current responses to account for dark current characteristics of the detector elements. An optical crosshair device can be mounted on the C-arm to project a visible crosshair co-axial with the source-detector axis and having a plane along the Y-axis and a plane normal to the Y-axis. The scan motion controller can move at least one of the C-arm and the table relative to the other to scan at least a first region and then a second region of a patient on the table with the fan beam along the Y-axis, wherein the first region and said second region are next to each other along the X-axis, each region has an edge overlapping an adjacent edge of the other region, and the distance along the Z-axis from an origin of the fan beam in the source to the table remains the same for the scan of each of the first and second regions. The system can use a merger responsive to outputs of the detector for scans of the first and second regions to merge detector outputs for positions of the fan beam which are spatially adjacent along the X-axis but are obtained at different times, into resulting merged detector outputs corresponding to detector outputs obtainable from a single fan beam having substantially twice the width of the fan beam emitted from the source. A source controller selectively pulses the source to emit therefrom single energy and dual energy x-rays in time-interleaved manner, and a processor is responsive to detector outputs for these single and dual energy x-rays to derive from them diagnostic information based solely on single energy x-rays as well as diagnostic information based on dual energy x-rays. A display coupled with the processor displays concurrently both the diagnostic information based on single energy x-rays and the diagnostic information based on dual energy x-rays. The scan motion controller moves at least one of the C-arm and the table relative to the other to carry out first a posterior/anterior or an anterior/posterior scan and then a lateral scan of a patient on the table without moving the patient between the two views. The scan motion controller rotates the C-arm around its rotation axis between carrying out the two scans, and selects the position of the source relative to the table for the lateral scan based on information respecting the patient's spine obtained in the course of the anterior/posterior or posterior/anterior scan. The scan motion controller stores scan sequences each corresponding to scanning a selected region of interest, or a selected set of regions of interest, in a patient on the table. An interface responsive to operator input selects a stored scan sequence, and the scan motion controller in response carries out the operator-selected scan sequence. A patient positioner is removably supported on the table and has: (i) a base for supporting the head and upper shoulders of a patient who is supine on the table; and (ii) a pair of wings spaced from each other along the X-axis and extending up from the base for supporting the patient's arms when the patient's hands are under the patient's head and the elbows are to the left and right of, and elevated from, the patient's torso. The patient positioner is shaped and dimensioned to maintain the patient's arms and hands away from the patient's chest and to straighten the patient's spine. A forearm positioner also can be removably supported on the table at a selected distance along the X-axis from an edge of the table. The forearm positioner comprises a base with an opening therein corresponding to a position for a patient's wrist when the patient's forearm extends along the Y-axis and is held against the table, and further comprises a fence against which the patient's forearm can be pressed to limit movement of the patient's forearm along the X-axis in a direction away from said edge of the table. The scan motion controller maintains the C-arm and the table at a selected relative position along the Y-axis while causing other relative motion between the C-arm and the table to obtain dual energy detector outputs for different relative positions between the C-arm and table while a patient is on the table. The system for such scanning can process the dual energy detector outputs to substantially cancel out soft tissue information while retaining bone information in the detector outputs, and can perform a computerized tomography image reconstructing bone structure but not soft tissue structure for which detector outputs have been obtained.

BRIEF DESCRIPTION OF THE DRAWINGS

A more complete understanding of the invention may be obtained from the following description when taken in conjunction with the drawings, in which:

FIG. 2B is a top view thereof.

FIGS. 4A and 4B are side elevational diagrammatic representations of the relative scanning motions made by the mechanical subsystems of an embodiment of the present invention and an equivalent motion thereof, respectively, when performing a whole-body scan.

FIG. 17 is a schematic perspective view of an optical crosshair line generating laser positioning aide of the present invention mounted in the examination table unit of the present invention.

FIG. 18 is a detailed schematic perspective view of the optical crosshair line generating laser positioning aide of FIG. 17.

FIG. 19 is a perspective schematic view of a forearm positioning aide of the present invention.

FIG. 20 is a an elevational view of the forearm positioning aide of FIG. 19, with a patient's arm positioned therein.

FIG. 21 is a plan view of the forearm positioning aide of FIG. 20.

FIG. 23a is an elevational view of the positioning aide of FIG. 22, illustrating a removable cover positioned over the aide.

DESCRIPTION OF A PREFERRED EMBODIMENT

Scanning System Overview

Figure 1:
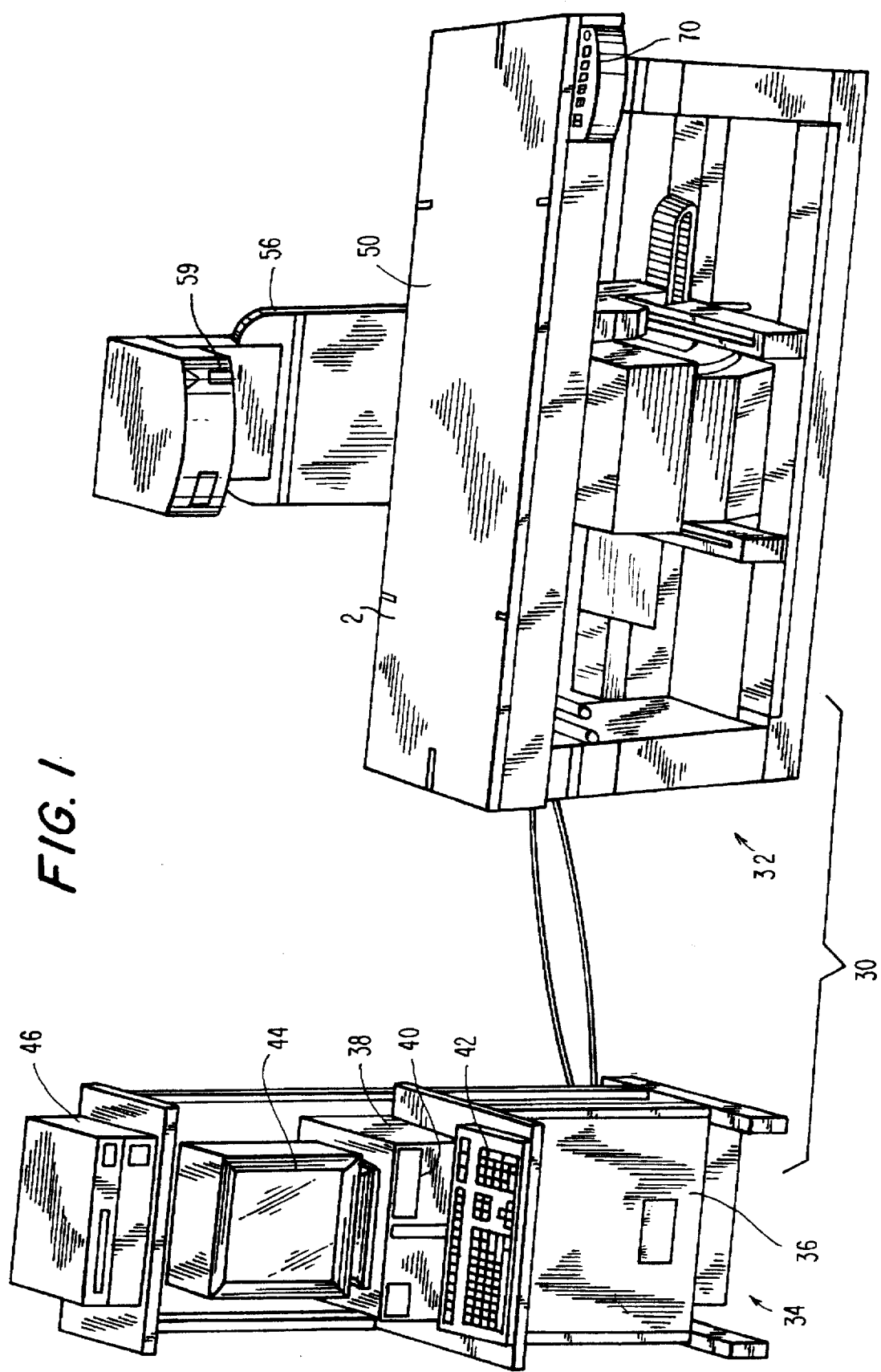
FIG. 1 is a diagrammatic representation of major subsystems of an embodiment of the invention.

Referring to FIG. 1, a scanning system 30 includes an examination table unit 32 comprising a patient table 50 and a C-arm 56 serving as a source-detector support. Examination table unit 32 contains electromechanical components, control systems and other components involved in performing a patient scan and acquiring scan data. Scanning system 30 also includes a workstation 34 which controls the examination table unit 32 and C-arm 56 and processes scan data into forms more useful for diagnostic purposes, such as into patient images and reports. Workstation 34 includes a system power supply module 36, a host computer 38 which has a floppy diskette drive recording device 40, an operator console keyboard 42, and a display monitor 44, and can include an optional printer 46.

Referring to FIGS. 2, 2A, 2B, 3A, 3B, 3C, 4A and 4B, a patient 48 can lie in the supine position during scanning on patient table 50. X-rays from an x-ray source 52 located beneath table 50 pass through patient 48 and are received by a detector 54 having an array of detector elements located above patient 48. Each detector element responds to x-rays at respective angular positions within a fan beam of x-rays. Both x-ray source 52 and detector 54 are supported on C-arm 56 which maintains a selected source-to-detector distance and alignment. In this example of the invention, x-ray source 52 has a stationary anode, and is a dual-energy (DE) pulse system that is synchronized to the alternating current system power source.

A slit collimator 58 is between source 52 and patient 48. Collimator 58 has one or more selectable slits machined or otherwise formed to allow the passage of x-rays through a slit from source 52 to patient 48, and is made of an x-ray opaque material, such as lead or tungsten, of sufficient thickness to substantially block the passage of x-rays through portions of the collimator other than the slits. For example, collimator 58 has a 1 mm wide collimator slit positioned an appropriate distance from the focal spot in source 52 and suitably aligned therewith. The x-ray radiation from x-ray source 52 passes through the slit in the collimator 58 and forms a fan shaped beam of x-rays 3a. The angle subtended by beam 3a and the distance between its origin at the focal spot of the x-ray tube and patient 48 are selected such that beam 3a would not cover the entire cross-section of a typical adult patient at any one time but would cover only a selected portion of that width. Collimator 58 can have several slits which are differently dimensioned and/or shaped, and can be provided with a mechanism for aligning any selected one of the several slits with source 52 and detector 54 to thereby select a desired shape for x-ray beam 3a. For example, each slit can be long along the X-axis and narrow along the Y-axis, the several slits can be in a row extending along the Y-axis, and the collimator with such slits can be moved along the Y-axis to align a selected one of the slits with the source and detector. In an alternative embodiment, collimator 58 can comprise a pair of x-ray opaque plates spaced from each other along the Y-axis to allow the passage of x-rays between them and thus to define the dimension of fan beam 3a along the Y-axis, and another pair of x-ray opaque plates spaced from each other to allow the passage of x-rays between them and thus to define the dimension of fan beam 3a along the X-axis. The two pairs of collimator plates are coupled with a control mechanism to selectively move them as required along the X-axis and the Y-axis to increase or decrease the dimension of fan beam 3a along the X-axis and/or the Y-axis. Fan beam 3a can have a fan angle of 22 degrees, whereas a fan angle of, for example, 65 degrees may be required to completely cover patient 48 for whole body analysis. Of course, x-ray beam 3a not only has width (along the X-axis illustrated in the Figures) but also has a thickness along the Y-axis that is defined by the width of the slit in collimator 58 (which can be, e.g., 1 mm) and distance from the origin of beam 3a. A scan line is defined by the portion of the patient imaged at any one time with fan beam 3a with detector 54, i.e. the width and thickness of the x-ray beam over which data is collected at one point in time. While the term scan line is used, it should be clear than this "line" in fact is a rectangle that has both a width in the x-direction and length in the y-direction. A complete pass or scan consists of a set of adjacent scan lines obtained over a period of time such that the entire region of interest has been measured. The scanning apparatus also has an x-ray beam modulator 60 which is between collimator 58 and patient 48 and can modulate x-ray beam 3a in a periodic pattern for certain types of diagnostic scanning. There is also an adjustable x-ray beam attenuator 62 for changing the intensity and/or energy spectrum of x-ray beam 3a as desired for different scans and/or other purposes.

System Scanning Motions

As seen in FIGS. 2 and 3A–3C, C-arm 56 rotates essentially within its own volume along rotational path R about a rotational axis extending along the Y-axis. In addition, C-arm 56 moves along the Y-axis, along the length of a patient and thus along the patient's spine. The Y-axis and the Q-axis labeled in FIG. 2 extend in the same direction. C-arm 56 includes a central portion 64 which can be formed of cast aluminum half rings machined to a required rolling radius and combined with an integrating structure to support x-ray source 52, slit collimator 58, x-ray beam modulator 60 and x-ray beam attenuator 62. A removable upper arm portion 66 houses x-ray detector 54, using a bracket interface. Thus, upper arm 66 may be removed for shipment in order to reduce shipping volume, and re-installed easily on site. A counter balancing system (not shown) is a part of C-arm 56, and is intended to minimize the external forces required to rotate that portion of the device as well as help balance C-arm 56, should a drive component fail.

Figure 2:
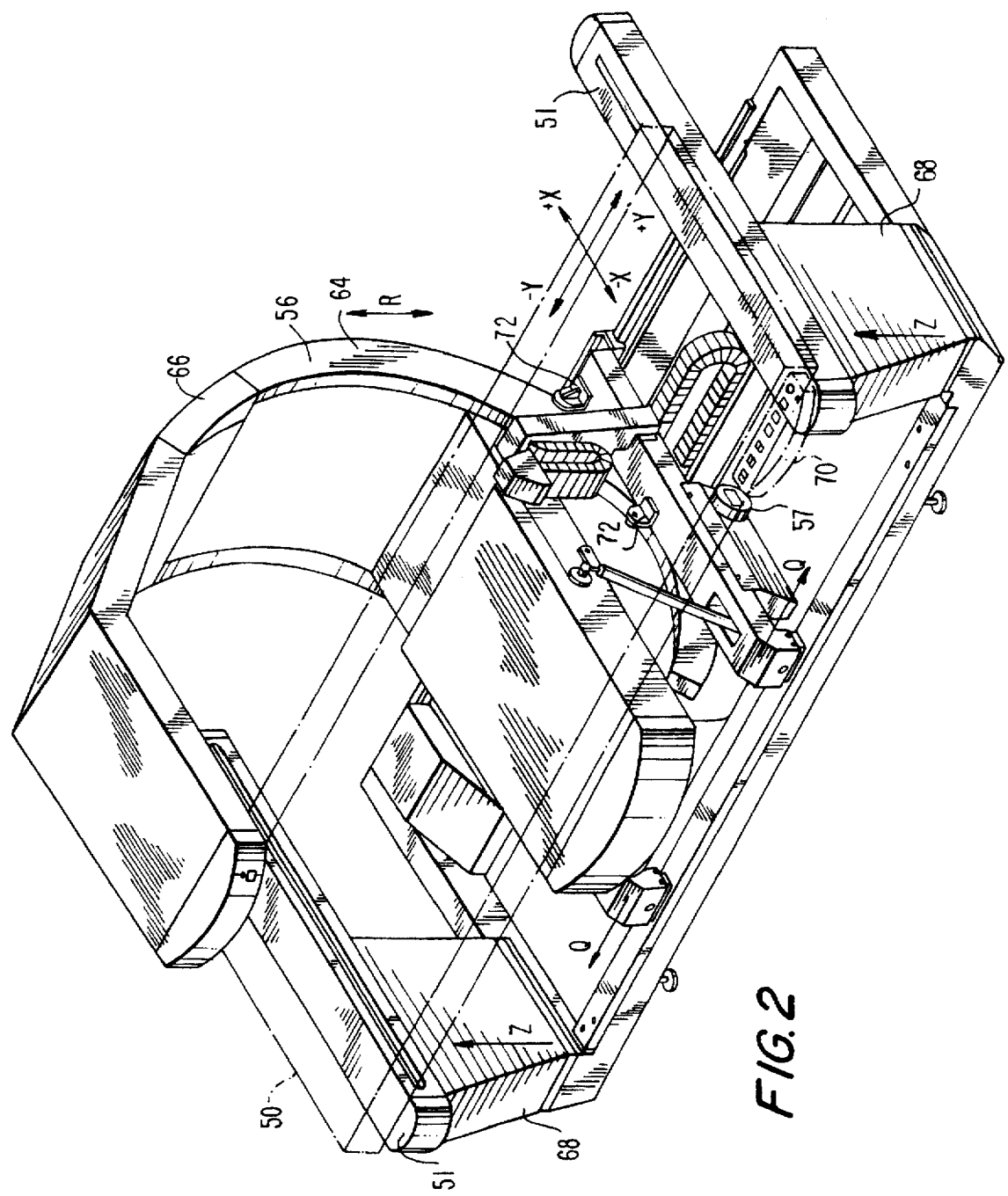
FIG. 2 is a diagrammatic representation of mechanical subsystems of an embodiment of the invention.
Figure 2A:
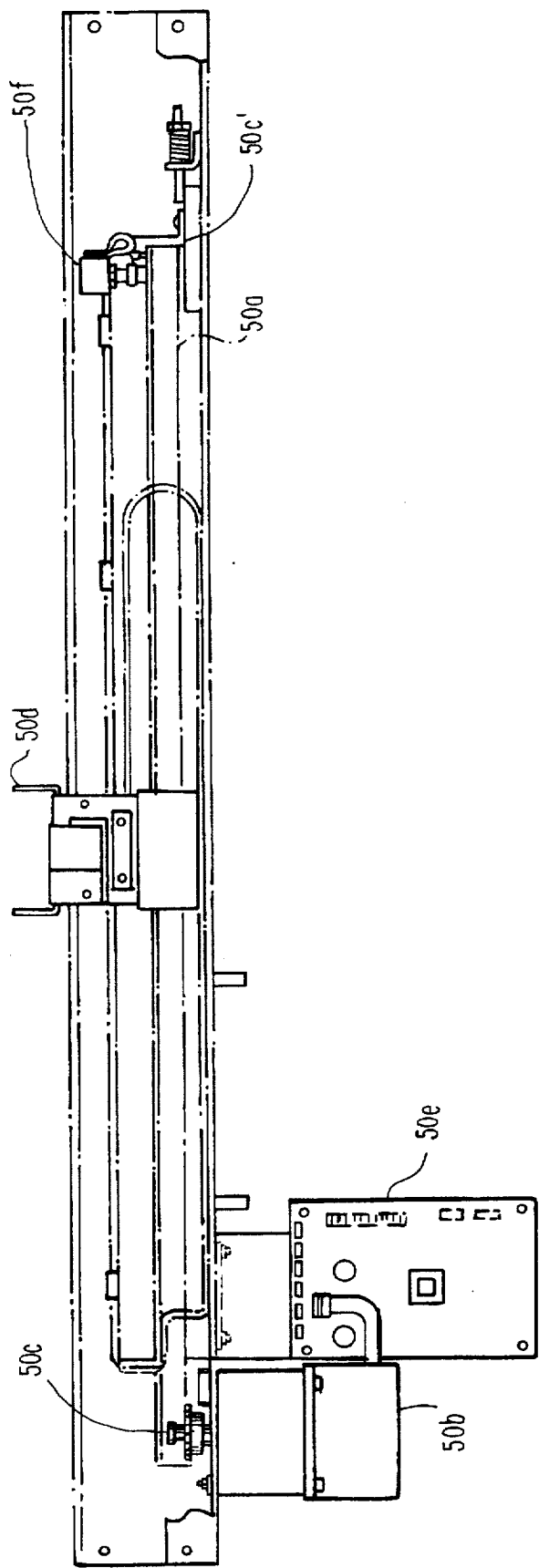
FIG. 2A is a front view of a diagrammatic representation of one of the motorized drive systems for the mechanical subsystems.

Patient support table 50, as seen in FIGS. 2, 2A and 2B, is translatable along all three axes—the longitudinal (Y axis), the transverse (X axis), and the vertical (Z axis). As seen in FIGS. 2A and 2B, table 50 can be driven in the positive and in the negative directions along the Y-axis by using a toothed drive belt 50a driven by a stepper motor 50b through a drive pulley 50c and an idler pulley 50c'. Belt 50a is secured to a table bracket 50d, which in turn is secured to table 50. A motor controller board 50e controls motor 50b. A DC servo motor can be used in place of stepper motor 50b, and other drive implementations can be substituted such as stepper-motor driven lead-screws. Each motion is computer controlled and monitored by an absolute encoder feedback system receiving feedback information from an absolute encoder 50f coupled with idler pulley 50c' to provide absolute information respecting any rotation of that pulley and thereby respecting any motion of belt 50a and table 50 in each direction along the Y-axis.

C-arm 64 moves in conjunction with patient table 50. The motion of table 50 makes it possible to achieve a more compact C-arm rotation volume. This can be seen by observing the geometric/volumetric motion requirements seen in FIGS. 3A, 3B and 3C. The motions of table 50 in the transverse and vertical directions (along the X-axis and along the Z-axis) help C-arm 64 clear table 50 when rotating between the three illustrated positions of C-arm 64 used for different types of patient procedures. In addition, the illustrated arrangement makes it possible to keep patient table 50 as close as practical to x-ray source 52 during posterior/anterior scanning while at the same time avoiding physical interference during rotation of C-arm 64.

As illustrated in FIGS. 4A and 4B, scanner system 30 makes it possible to scan the entire length of patient 48, or any selected region of the patient, as may be desirable in a "whole body" mode of operation, and at the same time keep the Y-direction motion of C-arm 64 shorter than would be needed if only C-arm 64 moved in the Y-direction. In this example, longitudinal scanning is accomplished by a combination of moving C-arm 64 along the Q axis (which is parallel to the patient table Y axis) and additionally moving patient table 50 in the longitudinal, or Y axis, direction. Each of C-arm 64 and table 50 moves a distance which is about half the total length of patient 48. This reduces the total length of the scanning apparatus and thus reduces the clinical floor space needed for the system. An illustration of this reduction in floor space requirement is seen when FIG. 4A is compared with FIG. 4B, which shows the motion that would be required for a comparable scan along the length of a supine patient if only C-arm 64 moved in the Q (or Y) direction and table 50 did not move in the Y-direction. This table 50/C-arm 64 compound motion keeps the overall length of the scanning apparatus 30 low when the system is not in the "whole body" scanning mode (and for those machines not having the "whole body" feature), to thereby reduce both installation size and shipping volume.

Another feature of scanning apparatus 30 is the method by which patient table 50 is elevated and lowered in the Z (vertical) direction, as shown in FIG. 2. Z-direction motion is accomplished using two independently motorized telescoping pedestals 68, one at each end of patient table 50. Synchronization is important to maintain the telescoping pedestals in a desired operating mode, e.g., always extended an equal amount. This is accomplished by employing an absolute linear encoder at each pedestal location, similar to encoder 50f discussed above. A computer which is a part of the system interrogates each encoder in pedestals 68 during motion and modulates the power to the faster pedestal to maintain the required synchronized motion by allowing the slower pedestal to catch up. This active synchronization is especially desirable in the case of AC motor driven pedestals, since speed tends to vary with load. Even with other motor driven types such as steppers, such synchronization can be of benefit, to ensure synchronous tracking even in the case of lost steps or other difficulties. The telescoping pedestals used in this apparatus have a dual nut drive as an additional safety feature, in case of drive failure. Each pedestal 68 can use a respective lead screw drive mechanism.

In addition, table 50 selectively moves left and right (as seen by a supine patient on table 50), along the X-axis. Table 50 is driven in each direction along the X-axis under computer control by motors and lead screw or belt mechanisms in the upper portions 51 of pedestals 60, using motor control and absolute encoder feedback as described earlier for the table motion along the Y-axis.

Figure 3C:
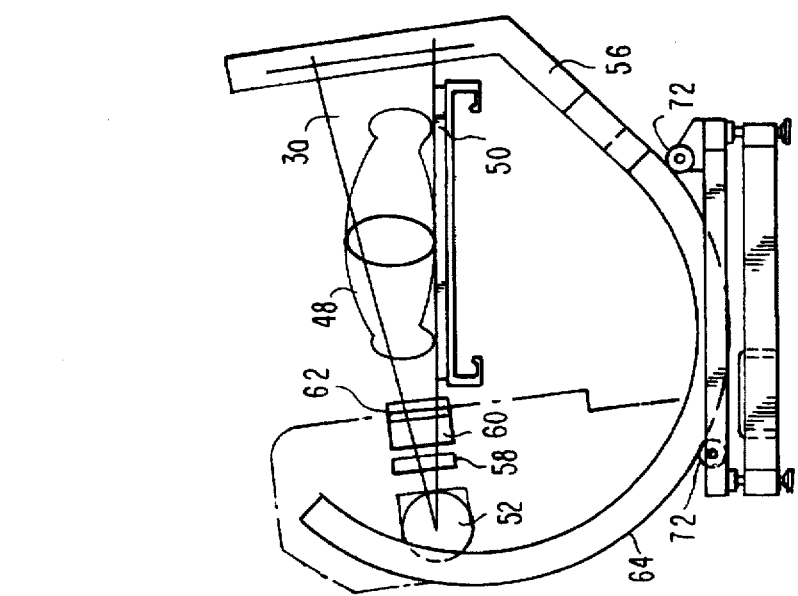
FIG. 3C is an end-on view for a lateral spine measurement.
Figure 3B:
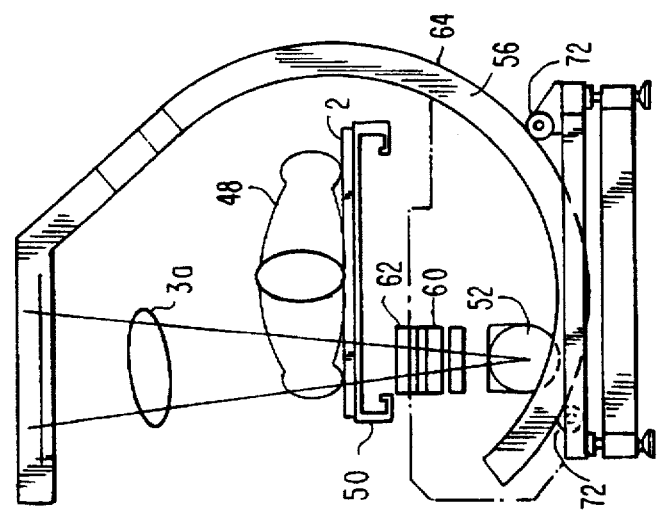
FIG. 3B is an end-on view for a hip measurement.
Figure 3A:
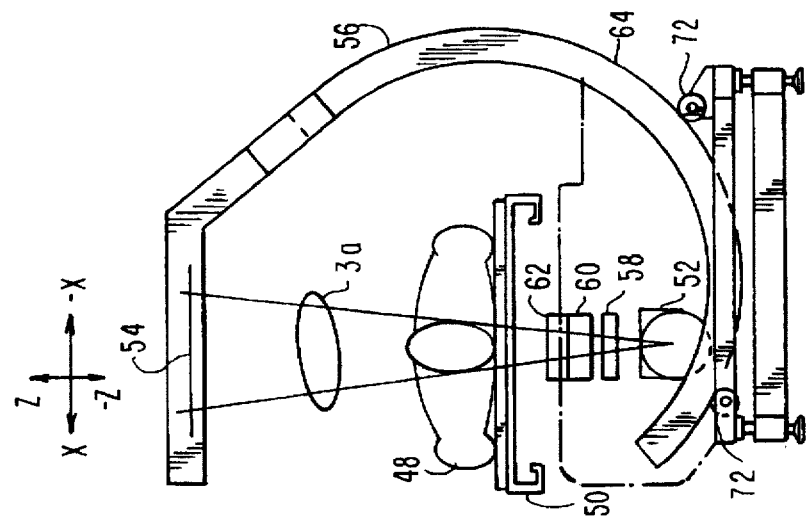
FIG. 3A is an end-on view of a patient table and a C-arm of the embodiment of FIG. 2, in the position to perform a PA (posterior-anterior) spine measurement.

C-arm 56 rotates about a rotational axis which extend along the Y-axis and is at the geometric center of portion 64 of C-arm 56. It is driven rotationally by a mechanism 57 (FIG. 2) and rides on rollers 72 (FIGS. 3A–3C).

Scanner 30 includes two automatic positioning modes—PATIENT ON/OFF & HOME—which are activated by buttons on a table mounted control panel 70 seen in FIGS. 1 and 2. The PATIENT ON/OFF function moves scanner table 50 and C-arm 56 to positions that make patient loading particularly convenient, e.g., C-arm 56 moves along the X-axis all the way to the left (as seen in FIG. 2) and patient table 50 all the way forward (in the minus X direction seen in FIG. 2) and centered along the Y-axis. The HOME function moves table 50 and C-arm 56 from their load positions (for the PATIENT ON/OFF mode) to position suitable for starting a PA spine scan.

As carried on C-arm 56, x-ray source 52 and detector 54 have a 2-axis motion with respect to patient 48 to carry out scans. Motion in the longitudinal Y (or Q) direction moves them along the patient axis as defined by the spine. A second motion, along the R rotational path, rotates them around the patient, the center of rotation being at a point C which is determined by the C-arm 56 and the method of rotation employed. The point of rotation is not the focal spot in the X-ray tube; rather, the center of rotation is spaced from the focal spot by a significant distance, and such spacing is important for the correct operation of the system. In the preferred embodiment, x-ray detector 54 and x-ray source 52, as carried by C-arm 56, rotate on a set of rollers 72. Thus, the center of rotation "C" is determined by the outer radius of C-arm 56.

As previously described, opposite x-ray source 52 is detector 54 which in this embodiment comprises approximately 200 detector elements arranged in a linear configuration extending along the X-axis in the XZ plane. Detector 54 is about 16" long in the X direction and is about 42" from the origin of beam 3a (42" source-to-detector spacing) and subtends a 22 degree fan angle. Alternately, the detector elements can be arranged along an arc centered at the focal spot in the X-ray tube. The detector elements that make up the array are silicon photo diodes coupled with a scintillation material, and they are fixed with respect to x-ray source 52. Other detector elements can be employed instead.

To perform a scan, a series of scan lines of data are acquired. To do this, C-arm 56, carrying x-ray source 52 and detector 54, moves along the Y-axis along the length of patient 48. This motion moves detector 54 and x-ray source 52 to form a succession of spatially overlapping scan lines adding up to a scanned rectangular area. The signals produced by the detector elements in detector 54 in response to x-rays impinging thereon at successive scan lines are digitized by an analog to digital (A/D) converter and are stored, for example on disk. The host computer 38 processes the signals from the A/D converter into density representations, and/or images, and/or reports of measured and/or calculated parameters, using principles disclosed in the material referenced in the background section of this disclosure.

For body structures of interest such as the spine, hip, forearm and wrist, only a single pass of fan beam 3a along the Y-axis may be needed because typically the area of interest in the patient's body is covered by fan beam 3a as shown in FIG. 3A for the Posteroanterior (PA) spine and in FIG. 3B for the hip. A similar scan can be performed on the forearm, as is done for the hip. Fan 3a has a sufficient angle to cover the entire forearm and/or wrist of a typical patient in a single pass, thus completing the scan in substantially less time than would be required for a pencil beam scanner in a raster fashion or by a narrower fan beam which cannot cover the entire forearm or wrist in a single pass. Indeed, in some circumstances a fan beam of only 14 degrees can be sufficient for the geometry of this embodiment to fully illuminate any of these body areas with x-rays. FIG. 3C shows the positioning for a lateral scan of the spine in which the view is orthogonal to the standard PA spine view. To attain this position, a series of movements of C-arm 56 and table 50 are carried out to ensure that the table and C-arm clear each other. In this embodiment, table 50 is moved along the X-axis and the Z-axis appropriately, while c-arm 64 is rotated about an Y-axis passing through point C until the desired lateral position is reached.

Figure 5A:
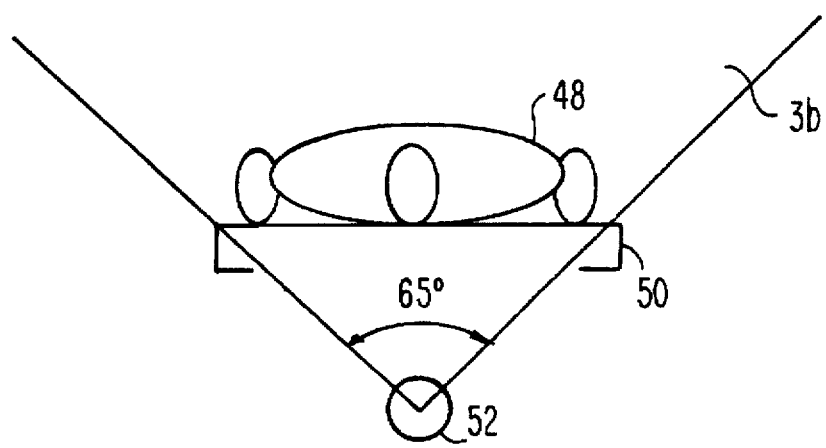
FIGS. 5A, 5B and 5C are representations of x-ray fan beam coverage of a patient for whole body measurement, illustrating the use of a wide fan beam made up of three passes or scans and involving notional rotation of an x-ray tube around the focal spot from which it emits x-rays.
Figure 5B:
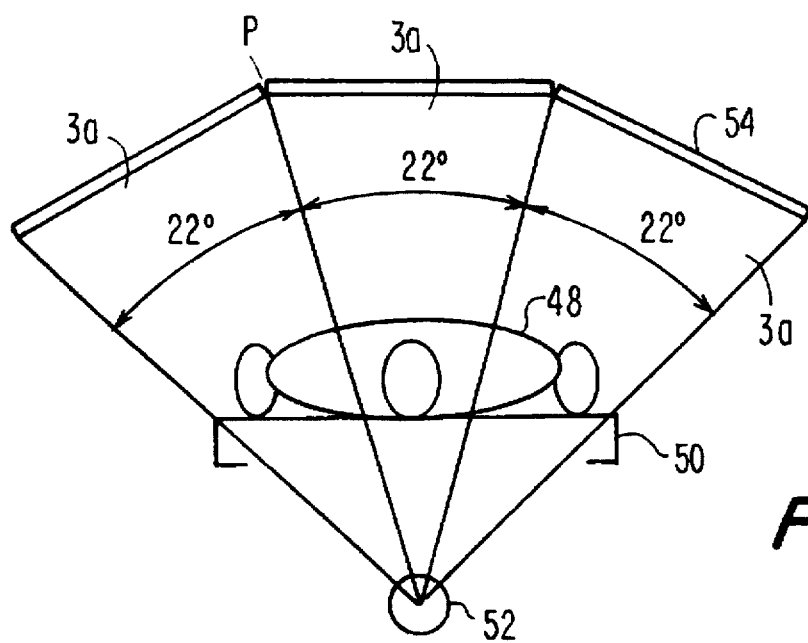

Whole body analysis can require that the-entire body be illuminated with x-rays. Referring to FIG. 5A, a fan beam 3b of approximately 65 degrees can be suitable for completely illuminating the entire cross-section of patient 48. As illustrated in FIG. 5B, this fan beam can be simulated by utilizing multiple passes with a smaller, 22 degree fan beam 3a as long as the fan beam for all of the passes maintains a selected focal spot to patient body relationship. With a fan beam 3a of 22 degrees and the nominal dimensions of the system in this embodiment, three passes along the Y-axis can be made to cover the entire patient 48. Thus, data from passes 1, 2 and 3 from the smaller fan beam 3a can be added together using a computer to provide data that is substantially equivalent to data that would have been obtained if one large fan beam 3b had been used. The conceptual illustration of FIG. 5B implies rotation of fan beam 3a with the focal spot thereof as the center of rotation. With fan beam 3a in a vertical orientation as in the middle position of fan 3a in FIG. 3B, fan beam 3a for pass 1 is rotated 21.5 degrees from the vertical while fan beam 3a for pass 3 is rotated -21.5 degrees from the vertical. The data from the 0.5 degrees of overlap is blended, e.g., by progressively using more of the data from the next pass as one moves in angle toward the next pass, using for example principle known in second generation CT technology.

Figure 5C:
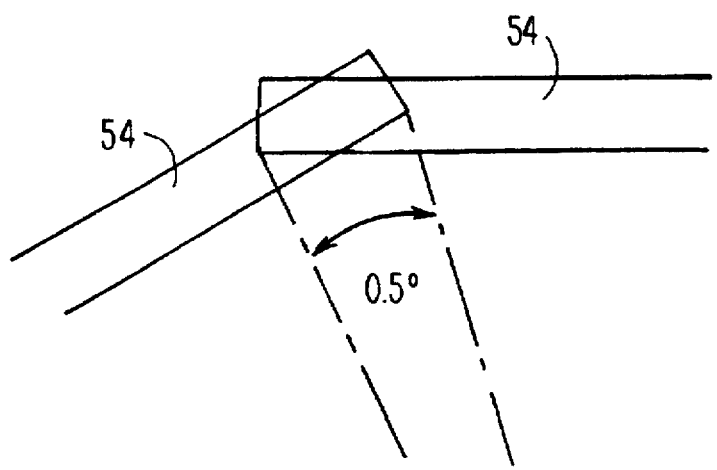

FIG. 5C shows an enlargement of the area designated P in FIG. 3B, where beams 3a for passes 1 and 2 overlap spatially. Fan beam 3a is slightly wider than the required 21.5 degrees so that there is an overlap of 0.5 degrees between the two passes. The overlapping areas imply that at least two different elements of detector 54 have measured the x-rays attenuated through the same body area.

If rotation of beam 3a around its focal spot, is desirable or practical, implementation of the multiple passes can be relatively easy because the only required motion between passes is rotation. However, in the preferred embodiment, the center of rotation C does not coincide with the focal spot. In accordance with the invention, the focal spot is made the effective center of rotation through motion of patient support table 50. In the system in accordance with the invention, C-arm 56 and table 50 can move with a total of five degrees of freedom. This feature is efficiently utilized in the whole body scanning mode.

Figure 6C:
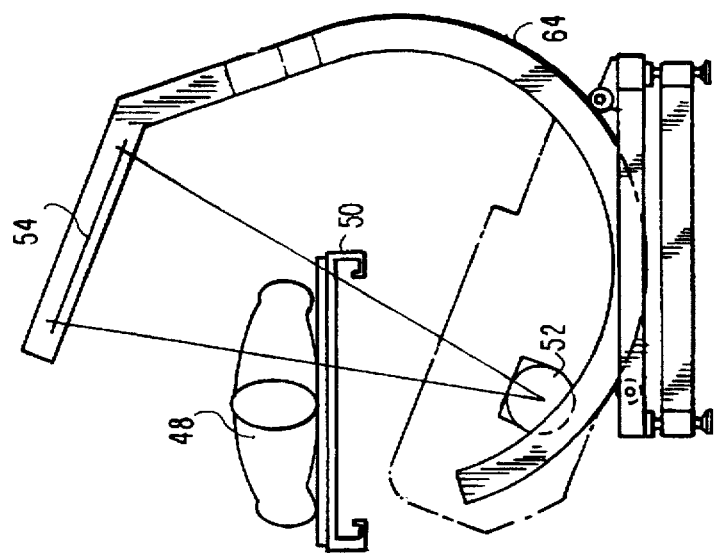
FIGS. 6A, 6B and 6C are end-on views of a preferred embodiment of the invention for whole-body measurement showing the C-arm/patient table positioning for three measurement passes or scans.
Figure 6B:
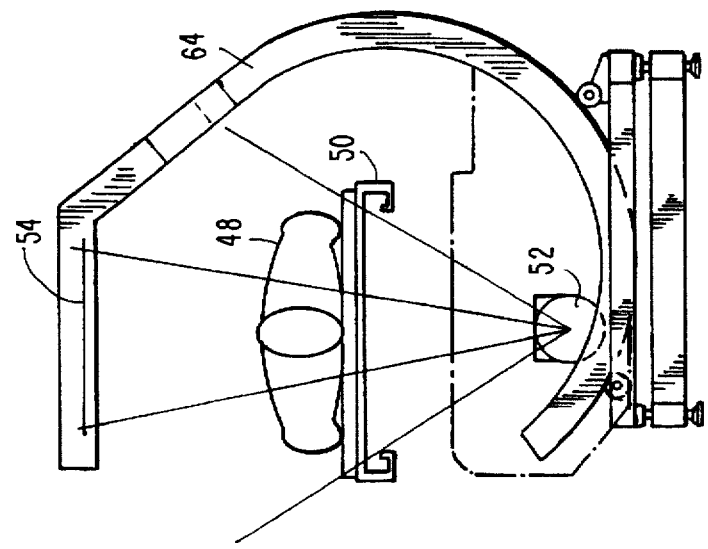
Figure 6A:
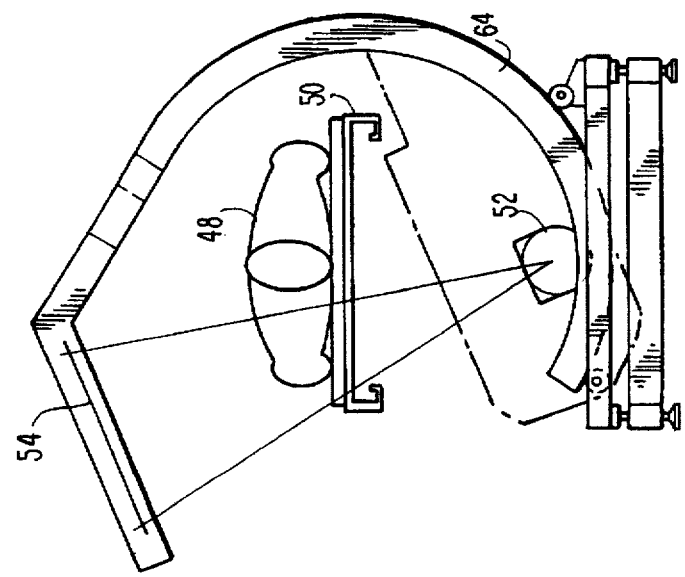

Referring to FIGS. 6A, 6B and 6C, the three views depict the relative positions of table 50 and C-arm 56 for three passes in the preferred embodiment of whole body scanning. Collimator 58 is not shown in these views. Each position maintains constant the spacing between the focal spot of beam 3a and table 50 as well as the location of a vertical intercept from the focal spot to table 50 relative to table 50.

Figure 7A:
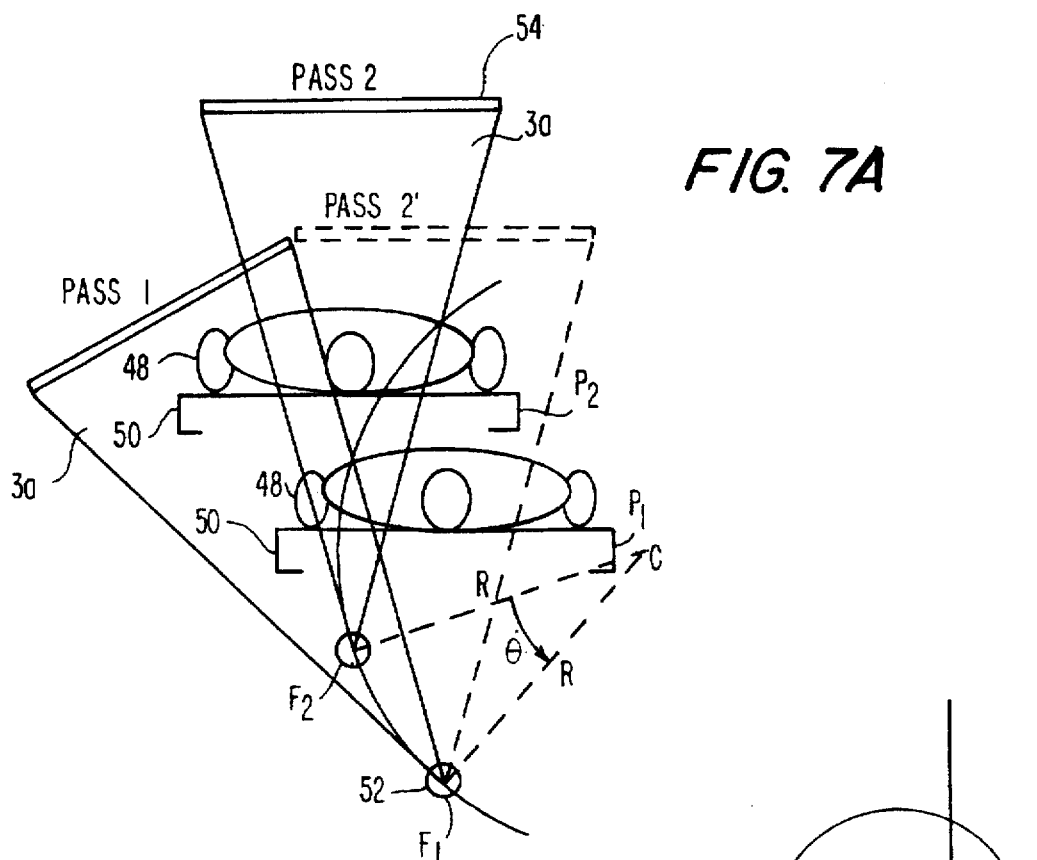
FIGS. 7A and 7B depict the relationship between the x-ray source and patient table position for two measurement passes in accordance with an embodiment of the invention.

FIG. 7A details the geometry of pass 1 in relation to pass 2. In pass 1, patient 48 lies supine on patient table 50 at position P1, and the focal spot of x-ray source 52 is at F1. In this position, only the left side of patient 48 is illuminated with x-rays within fan beam 3a. If C-arm 56 could now be rotated about the focal spot, the conditions of pass 2' would be achieved in which the central part of the patient 48 would be illuminated. However, the focal spot rotates about the center of rotation of C-arm 56 located at C with a radius R. A rotation through an angle of −θ about a pivot axis at point C attains the positioning of pass 2 in which the focal spot is located at F2. To maintain the focal spot of beam 3a at the desired position relative to the patient, patient table 50 moves to position P2 (without moving patient 48 relative to table 50). At position P2, the spatial relationship between F1 and P1 are identical to the spatial relationship between F2 and P2, i.e., a vertical drawn from the focal spot intersects-patient table 50 at the same point and extends over the same distance. To attain position P2 requires two motions of table 50, one over a distance DX along the X-axis and another over a distance DZ along the Z-axis. These two motions can be consecutive or concurrent (or can overlap in time only in part). These distances DX and DZ correspond to the differences in X and Z coordinates for focal spot positions F1 and F2.

Figure 7B:
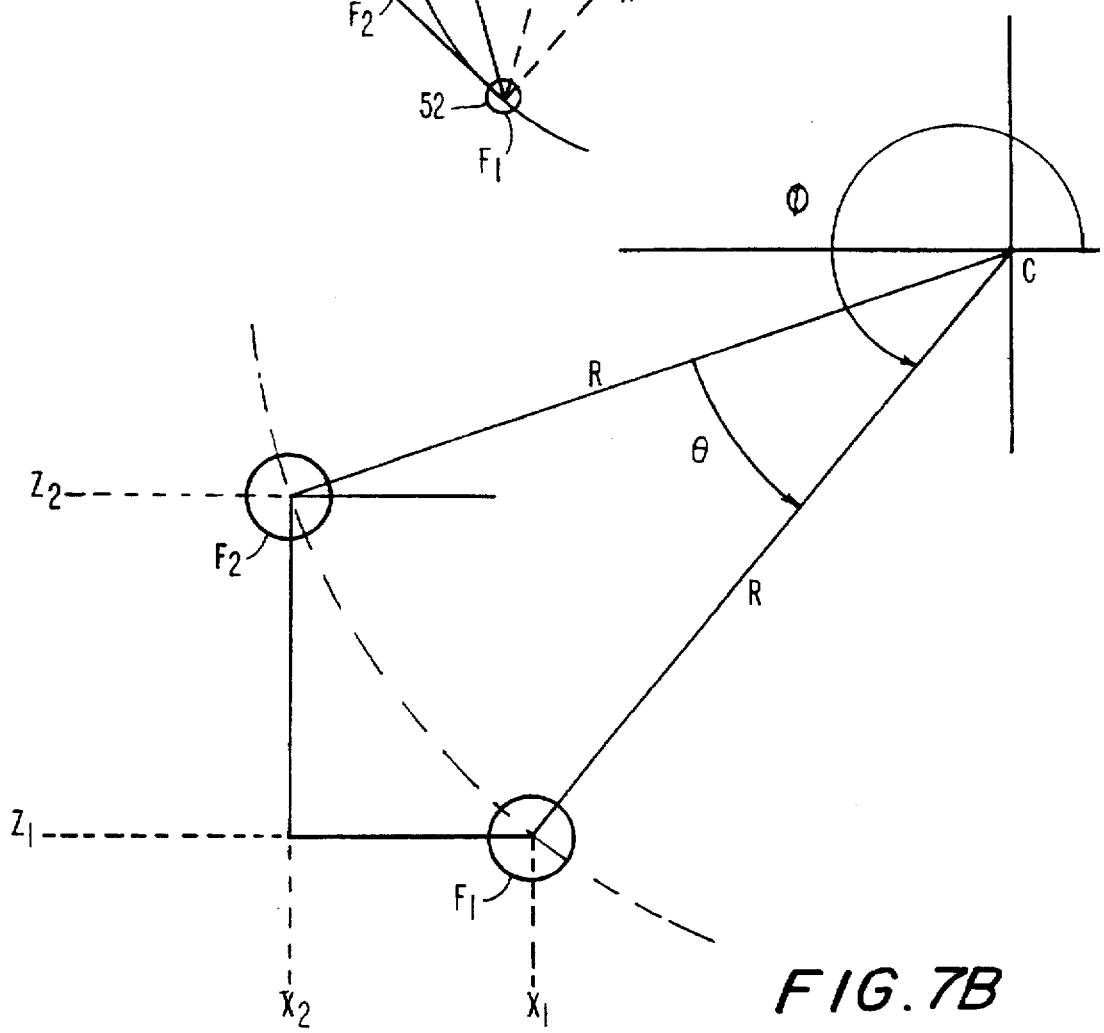

Referring to FIG. 7B, where the terms are graphically defined, the distances DX and DZ are given by the relationships:

$$DX=(X2-X1)=R[\cos \phi(\cos \theta -1)+\sin \phi \sin \theta]$$

$$DZ=(Z2-Z1)=R[\sin \phi(\cos \theta -1)-\cos \phi \sin \theta]$$

Patient table 50 is translated along the X-axis over a distance DX and along the Z-axis over a distance DZ, where φ is the angle that F1 makes with the center of rotation C as the origin and θ is the angle of rotation between F1 and F2 which in the preferred embodiment is about −21.5 degrees, with the negative angle denoting a clockwise rotation around C between passes 1 and 2. Similarly, for pass 3, the focal spot is translated by DX and DZ with θ=−43 degrees.

Figure 8:
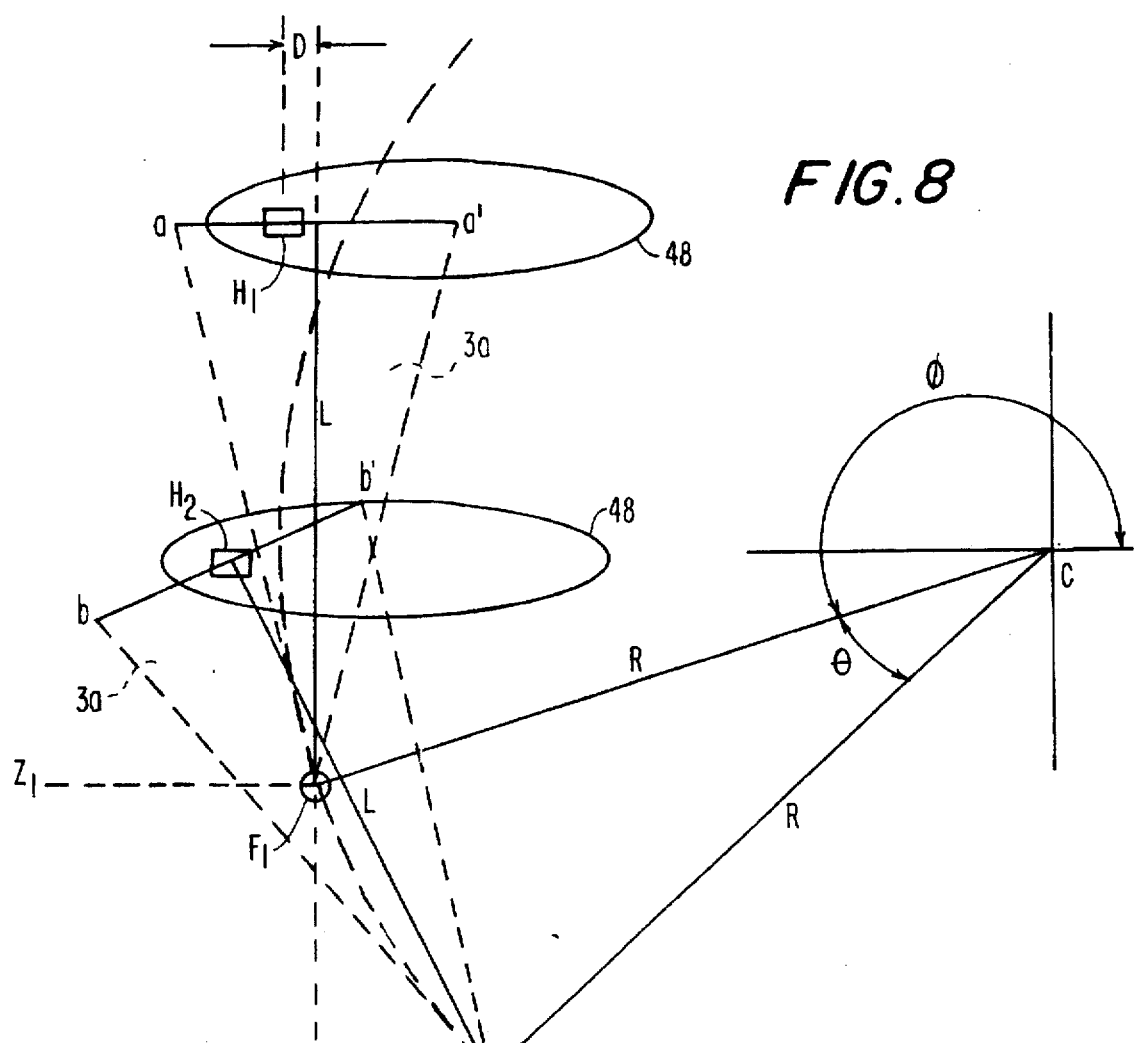
FIG. 8 depicts the relationship between the x-ray source and the patient table for an oblique hip measurement in which the x-ray beam is angled relative to the patient in a manner similar to that illustrated in FIGS. 6A and 6B.

As illustrated in FIG. 8, an additional analysis called the "oblique hip" can be performed in accordance with the invention by suitably rotating C-arm 56 and translating patient table 50 along the X-axis and the Z-axis. The actual position can be determined beforehand by performing a "scout" scan which is usually a high speed, low dosage scan for the PA hip. In FIG. 8, F1 is the location of the focal spot of beam 3a, and line a–a' represents the field of radiation in patient 48, at a distance L from the focal spot of beam 3a. For convenience and clarity, patient table 50 is not shown in FIG. 6, but its position can be seen in FIG. 6A. A hip designated H1 is offset from the central ray of beam 3a by a distance D which can be quantitatively determined from the scout scan. Upon rotation of C-arm 56 through an angle θ (or 23 degrees in the preferred embodiment) the focal spot is now at F2. Table 50 is translated along the X-axis and the Z-axis while patient 48 remains stationary on table 50 so that the patient's hip is at position H2 which is now located in the central ray F2–H2 of the radiation field b–b' in patient 48. In this geometry, the X and Z translations, DX and DZ, of table 50 made to place the hip at H2 are given by the relationships:

$$DX = R \cos \phi [\cos \theta - 1] - \sin \phi [R \sin \theta - L] + D$$

$$DZ = [R \sin \phi + L][\cos \theta - 1] + R \cos \phi \sin \theta$$

where R is the distance of the focal spot F1 from the center of rotation C of the focal spot of beam 3a, and φ is the angle of the focal spot F1 with respect to the center of rotation C. The distance L from the focal spot to the hip is estimated as the sum of the known distances from F1 to the table plus the estimated distance from the table to the field a–a'.

X-Ray Beam Reference and Modulation System

Figure 9:
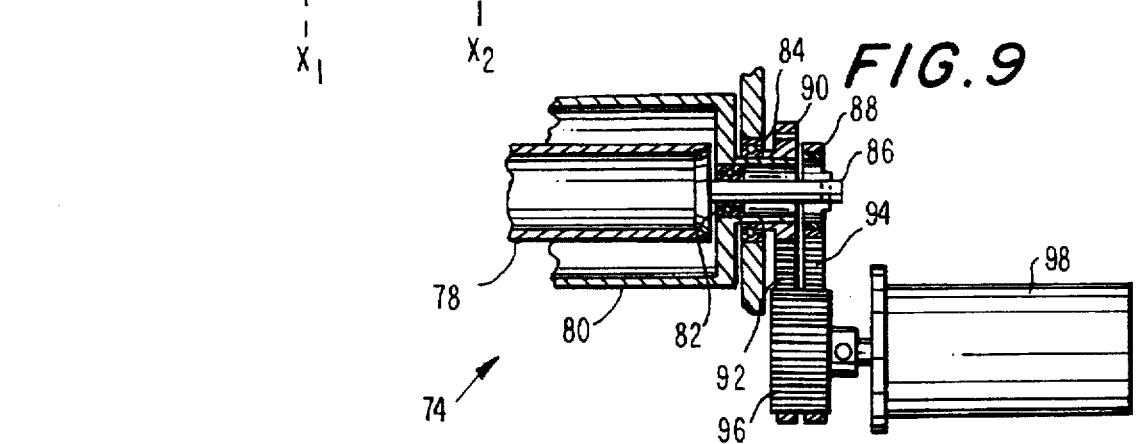
FIG. 9 is a schematic axial view of a coaxial x-ray modulator of the present invention, shown in partial cross section.
Figures 12A, 12B:
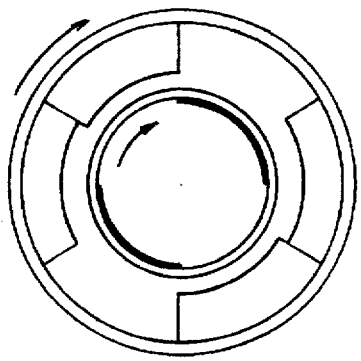
FIGS. 12A–12F show respectively the six rotational combinations of x-ray modulators which may be utilized in the present invention.
Figure 12C:
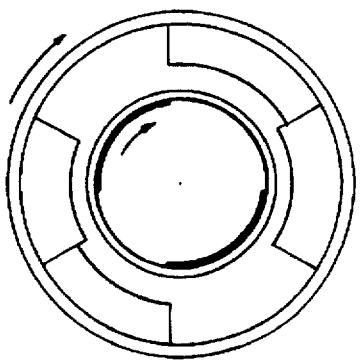
Figure 12F:
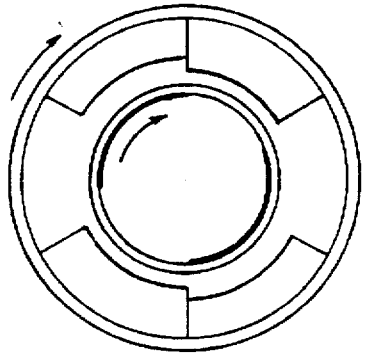
Figure 12E:
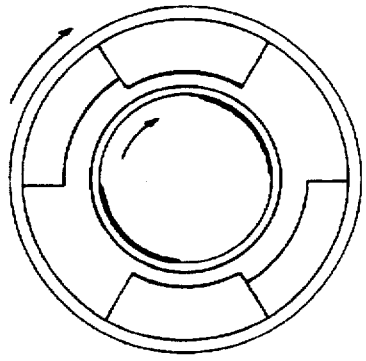
Figure 12D:
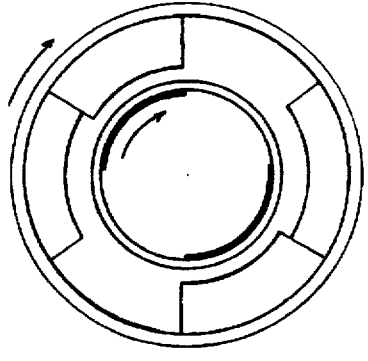
Figure 11:
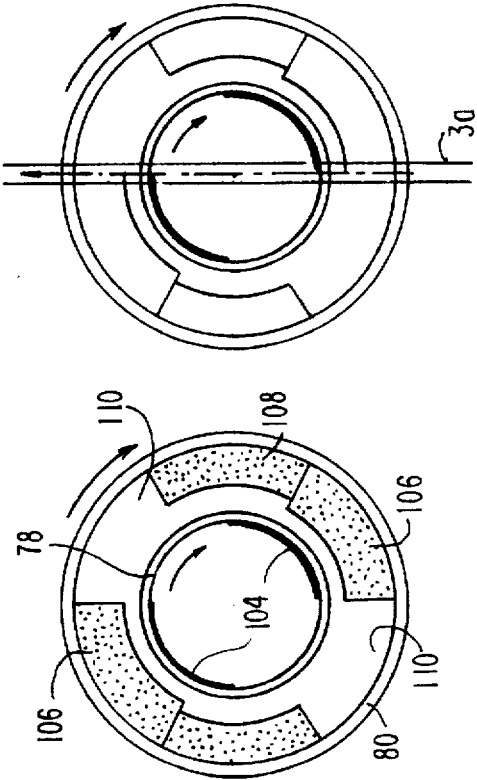
FIG. 11 is a schematic radial view of the x-ray modulator of FIG. 9, shown in a dual-drum configuration.
Figure 10:
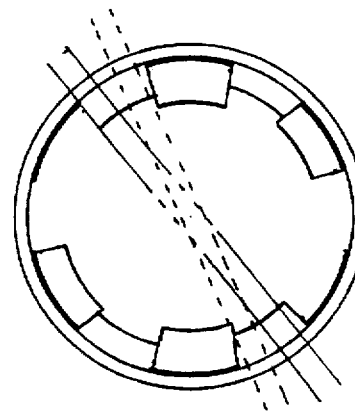
FIG. 10 is a schematic radial view of the x-ray modulator of FIG. 9, shown in a single-drum configuration.
Figure 13:
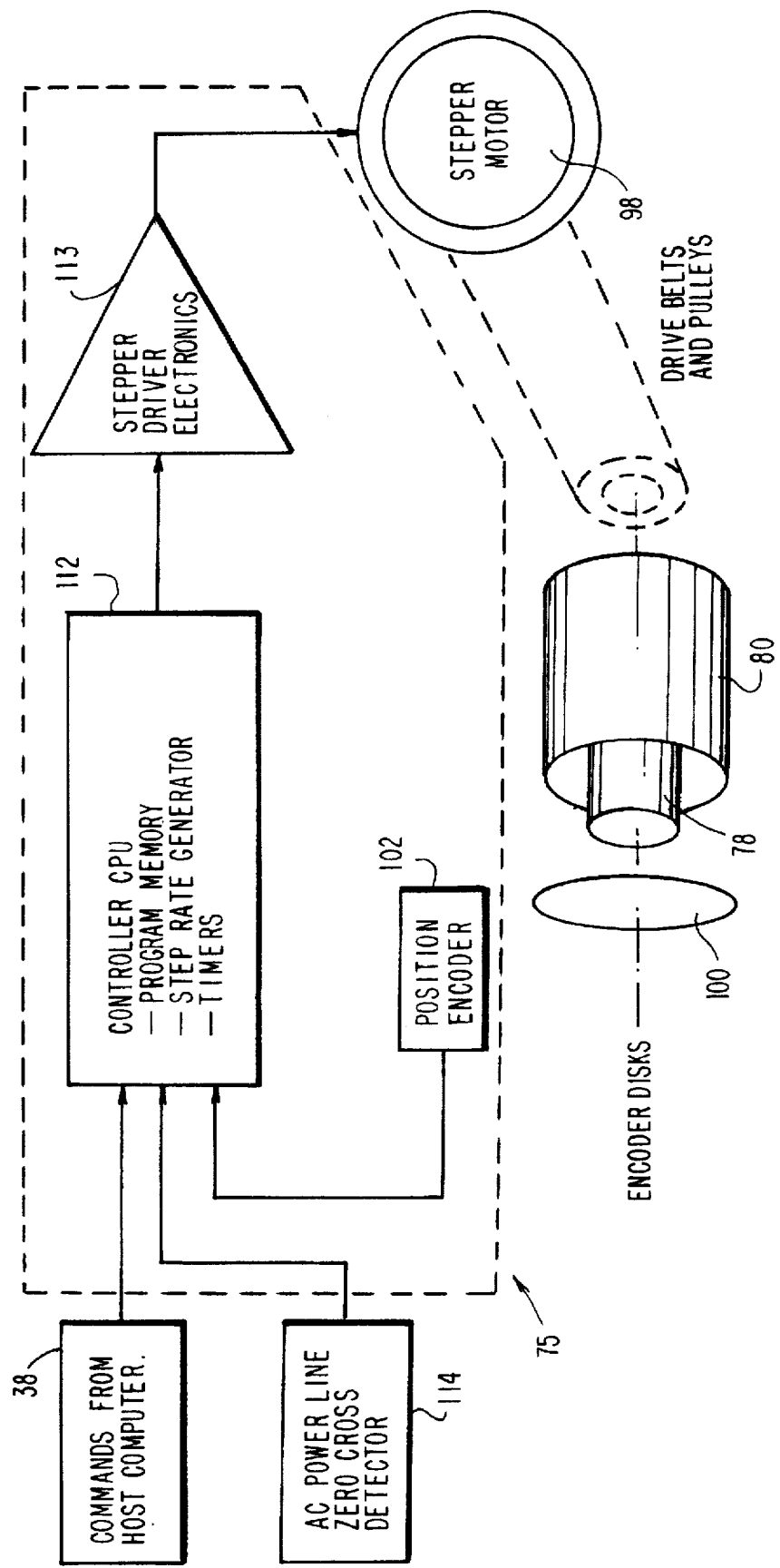
FIG. 13 is a controller block diagram for the x-ray modulator of FIG. 9.

A reference and modulation system 60 comprises a drum assembly 74 seen in FIGS. 9, 10 and 11, and a control system 75 seen in FIG. 13. Drum assembly 74 can use one nested cylinder 76 (FIG. 10) or two or more nested cylinders 78, 80 (FIGS. 9 and 11), or other shapes. System 60 is a three-dimensional rotating assembly, using support bearings for each rotating drum, drive shafts, rotational position encoders, drive belts, drive motors with related pulleys, and attenuation material of different types arrayed in a pattern within the inner periphery of one or more drums. Control system 75 includes a controller which receives positional signals from an encoder and issues drive commands to the drive motor system.

Referring to FIGS. 9 and 11, drum assembly 74 has a pair of nested, preferably coaxial, hollow inner and outer cylinders 78, 80, respectively, on separate bearing sets 82, 84, respectively, which allow the cylinders to rotate freely relative to each other. Shaft 86 for inner cylinder 78 does not extend into that cylinder, so that its center remains hollow. Respective toothed pulleys 88, 90 are mounted on an end of each cylinder 78, 80, and they are connected via timing belts 92, 94 to a single drive pulley 96 mounted on the modulator drive motor 98. The preferred ratios for pulleys 88, 90, 96 are such that outer cylinder 80 would make one turn for three turns of inner cylinder 78, e.g., the ratio of pulleys 96 and 80 is 1:1 while the ratio of pulleys 96 and 88 is 1:3. Drive motor 98 can be a two-phase, pulsewidth modulated (PM) stepper motor, such as one having 200 steps per revolution.

As seen in FIG. 13, encoder disks 100 and position encoders 102 (only one is shown for conciseness) for measuring the angular position of each respective cylinder 78, 80 are mounted at the opposite end of the drive system. Both encoders 102 and motor 98 are coupled to control system 75.

Within the inner periphery of each drum are the reference and filtering attenuation materials which are curved to match the drum inner radius so that the path length of the x-rays through these materials would be the same everywhere for any one attenuation material. The attenuation materials may be profiled to match the center of the fan beam radius, in order to further equalize the path length of material traversed by the x-ray beam. As seen in FIG. 11, inner cylinder 78 is divided into four 90 degree sections, with two brass strips 104 located 180 degrees across from each other. As inner cylinder 78 rotates, a sequence of: brass, air, brass, air, etc., at 50% duty cycle is generated. Both the brass and non-brass segments also contain the cylinder wall material, so the additional attenuation value of the cylinder wall material may be accounted for through scan data normalization.

Outer cylinder 80 is divided into six, 60 degree segments. At two opposing segment locations are mounted bone simulating materials 106; another pair of opposing segments have tissue simulating material 108, and the last two locations are left empty and referred to as air segments 110. Rotation of outer cylinder 80 therefore creates the following periodic sequence: bone, tissue, air, bone tissue, air, etc. As seen in FIGS. 12A–12F, when both cylinders 78, 80 rotate in accordance with the previously defined cylinder rotational ratios, x-ray beam 3a passing through the center of rotation would be modified by the following sequence of attenuation materials: bone+brass; bone+air; tissue+brass; tissue+air; air+brass; air+air; followed by a repeat of the same pattern for the second half of the outer cylinder.

Because the segments of like attenuation reference materials are located 180 degrees opposite of each other, the x-ray beam traverses both pieces at the same time, eliminating the need to have the pieces critically matched. Another benefit of the coaxial drum 74 geometry is the minimization of the transition angle, defined as the angle during which a non-zero width x-ray fan beam spans the edges of two material segments. The x-ray beam content is changing during the transition angle and is not desirable for patient scan measurements.

If desired, one, two or more cylinders may be nested, to vary the number of attenuation material layers which intercept the beam path.

Modulator control system 75 is illustrated in FIG. 13 and comprises a circuit board having a microcomputer CPU 112 and interface circuitry. Control programs for operating microcomputer 112 are stored in electronic memory, such as for example an EPROM memory device. A suitable microcomputer is the model 80C320 manufactured by Motorola. It should be understood that other microcomputer architecture could be utilized to operate the controller. Control system 75 can be implemented in hardware only, without a CPU, or other known types of control systems can be used having combinations of hardware and software processing, so long as they are capable of operating the modulator system in accordance with the control parameters described in this specification. Inputs to the system are commands from the host control computer 38; AC power frequency timing information from zero crossing detector 114; and positional encoder 102 signals from drum assembly 74. Control system 75 outputs are motor 98 step pulses to stepper driver electronics 113 and system status information to host control computer 38.

In operation, the rotational axis of modulator drum assembly 74 is positioned along the long axis of the x-ray fan beam 3a through mechanical alignment.

As x-rays within fan beam 3a travel from source 52 toward detector 54, they pass first through one wall of outer cylinder 80, then through the material mounted on the inside of outer cylinder 80, then through the wall of inner cylinder 78, then through the material mounted on the inside of inner cylinder 78, and so on, until beam 3a exits the other wall of outer cylinder 80, as shown in FIGS. 12A–12F. When the two cylinders 78,80 are stationary, x-ray beam 3a is modified by the composite stack of materials present in its path. When cylinders 78, 80 are rotating, a sequence of different material combinations are inserted into the path of x-ray beam 3a in a periodic, repetitive fashion, as determined by the CPU-control 112 directing the drive motor system. The sequence and/or timing of the material combinations which attenuate beam 3a can be modified by changing controller programming.

Figure 14:
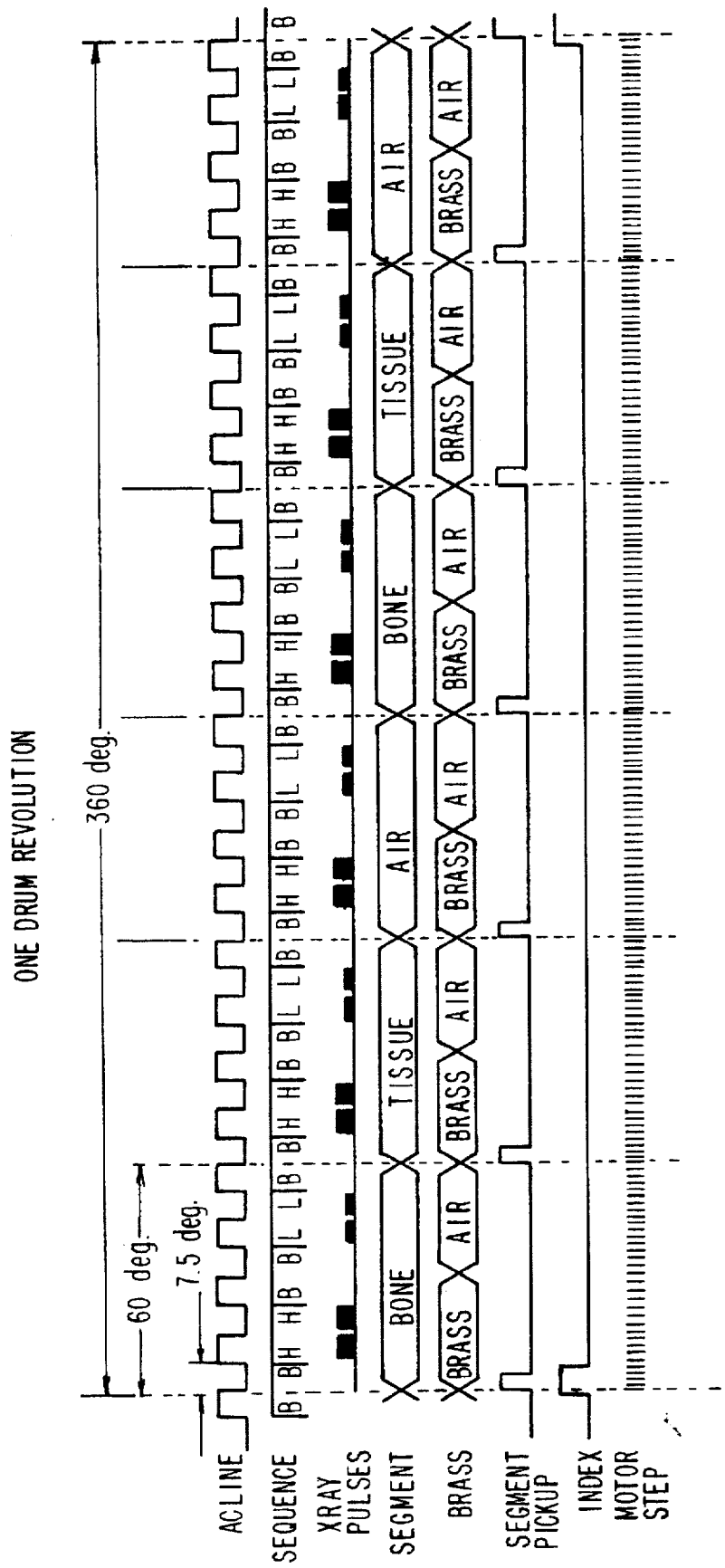
FIG. 14 is a timing diagram for the dual-drum x-ray modulator of FIGS. 9 and 11.

Through the use of the above-described ratios of modulator drive system pulleys 88, 90, 96 and through the use of suitable parameters for stepper motor 98, the system in accordance with the invention can achieve the timing relationships between pulses of x-fay source 52 pulse and positions of inner cylinder 78 and outer cylinder 80 illustrated in the timing diagram of FIG. 14.

Attenuator Selection and Positioning Mechanism

Figure 16:
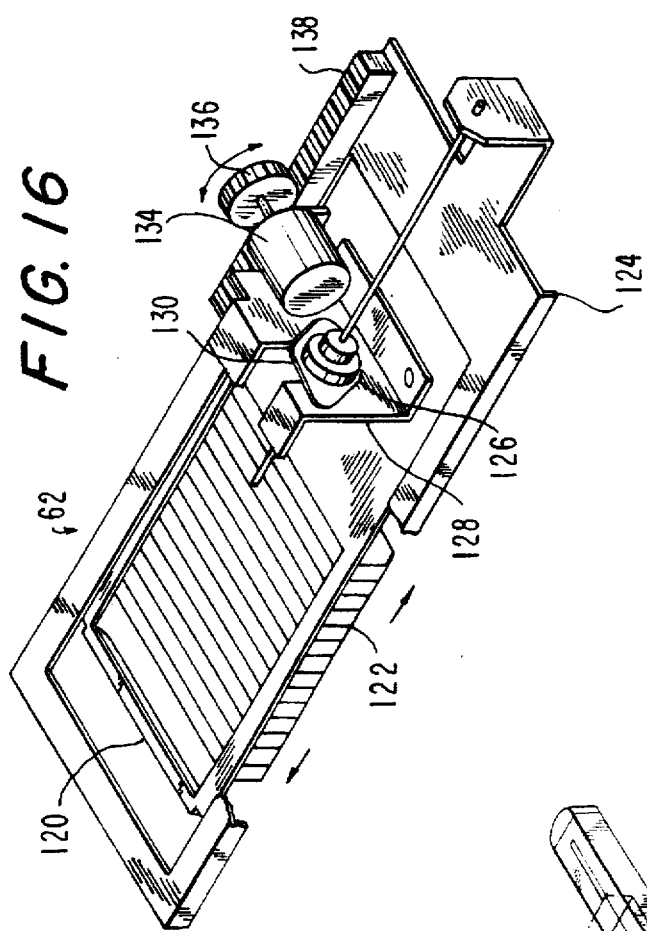
FIG. 16 is a detailed schematic perspective view of the attenuator selection and positioning mechanism of FIG. 15.
Figure 15:
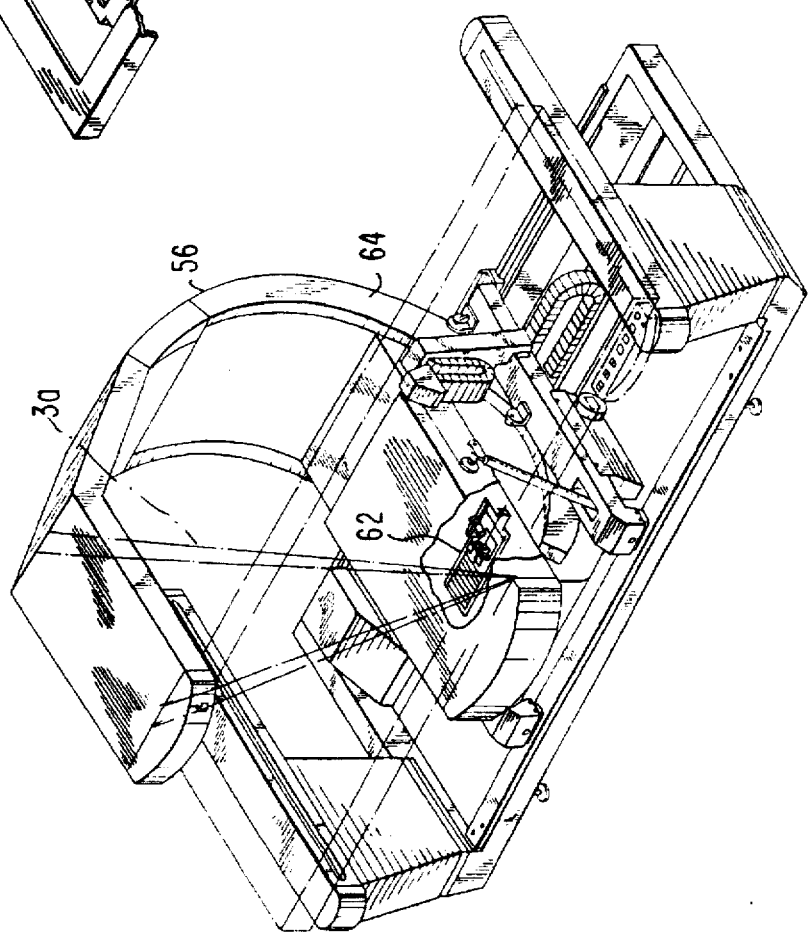
FIG. 15 is a schematic perspective view of an attenuator selection and positioning mechanism of the present invention mounted in the examination table unit of the present invention.

FIGS. 15 and 16 illustrate the x-ray attenuator selection and positioning mechanism 62 which is between x-ray source 52 and x-ray detector 54. The x-rays within fan beam 3a pass through attenuator mechanism 62, so that the effective beam intensity and/or energy (spectrum) are influenced by whatever attenuating medium is placed within the beam path.

Attenuator selector mechanism 62 includes a movable support plate 120 which houses a number of materials 122 of varying thickness, physical attenuation properties, or both, as desired or required for the imaging procedures to be performed by system 30. As seen in FIG. 16, materials 122 can be arrayed next to each other in the Y direction, with each individual material extending in the X direction. Alternatively, other array patterns can be selected, such as a radial, planar, or a three dimensional array that envelops the x-ray source 52. However, a flat planar array of sequentially placed materials, similar to a laminated butcher block table, provides for cost effective manufacture within a small, flat package. Low system profile of the selector mechanism, located as close as practical to the focal spot in x-ray source 52, reduces the physical size required for each block of attenuating material to cover the entire imaging beam 3a, thus reducing material cost and weight. Support plate 120 is supported by and slides on main drive plate 124, which in turn is coupled to C-arm 56. The relative fit of support plate 120 and drive plate 124 provides lateral alignment of the attenuation materials relative to x-ray beam 3a.

Support plate 120 in attenuator mechanism 62, and the attached array of different attenuating materials 122, are coupled to a drive mechanism 126 for translation relative to radiation beam 3a. As seen in FIG. 16, drive mechanism 126 includes a motor bracket 128 attached to sliding support plate 120. A linear motor 130 is attached to motor bracket 128 and a drive screw portion 138 of a linear motor is rotatively attached to main drive plate 124, to cause the relative sliding motion between main drive plate 124 and support plate 120. Other suitable drive mechanisms can include a rotary stepper motor with a cogged belt drive, worm gear mechanism, drive screw mechanism as used in machine tool beds, or any other type of known drive system which can provide the desired relative sliding motion between support plate 120 and main drive plate 124. It is also possible to utilize a manual drive mechanism, such as a screw jack cranked by the machine operator. A rotary encoder 134 is attached to motor bracket 128. This rotary encoder 134 has a pinion gear 136 interacting with a gear rack 138 mounted on main drive plate 124. In this manner, the rotary position output of encoder 134 can be correlated to the position of a specific attenuation material 122 relative to radiation beam 3a.

A controller 140 (see FIG. 24) reads the output signal of attenuator mechanism encoder 134 and also provides drive signals for actuation of linear motor 130, in a manner similar to that discussed in connection with x-ray beam modulation system 60. Thus, when the scanner operator selects a desired attenuation material 122 by way of the scanner control system, the scanner automatically aligns the desired material 122 relative to the radiation beam path 3a. Alternatively, other motor control and drive systems well known in the art may be utilized in connection with the attenuator drive mechanism.

Optical Crosshair Line Generating Laser Positioning Aide

The x-ray system described herein has the capability of measuring various anatomical regions, and includes an optical crosshair device which helps the operator position the patient on table 50. The operator uses the crosshair device to ensure that the x-ray beam will be directed to the desired anatomical region, that different scans will register correctly with anatomical features or with each other, and that scans of the same region but at different times will register well. Accurate positioning helps avoid the need to interrupt a procedure when it becomes apparent that the measurements being obtained are not for the desired anatomical region, or to repeat procedures for similar reasons. It also helps achieve reproducible positioning of the anatomy, allowing baseline scans to be used reliably for subsequent scan evaluations.

As illustrated in FIGS. 17 and 18, a single line projection laser 152 is the source of the laser beam. When C-arm 56 is in the position illustrated in FIG. 17 (for a posterior-anterior scan), the laser beam is directed downward, creating a visual crosshair beam 160 consisting of two fan beams of laser light approximately ninety degrees to each other. Crosshair beam 160 can illuminate a patient, or the top of table 50, or a calibration device. Although the laser is low voltage the line quality of crosshair 160 is bright and crisp, even in a well lit room. The low profile, tri-pod adjustment, and internal shutter permit the laser to be installed in tight fitted areas but still allow for ease in adjustment or replacement.

The optical crosshair device is constructed of a one piece base 144, two optical mirrors 146, 148, a beam splitter 150, one optical line generating laser 152, and a internal mechanical shutter 154 with an external slide 156, allowing the operator or the patient to block the laser beam. The external tri-pod adjustment 158 permits initial laser alignment to the array and the source. The Y axis fan beam of laser light of crosshair 160 aides in aligning the patients spine along the Y axis of the x-ray apparatus. The X axis fan beam of laser light of crosshair 160 helps align the hips perpendicular to the spine and thus to the Y axis of the x-ray apparatus.

Forearm Positioning Aide

For a wrist or forearm scans, it is desirable that the patient's wrist and/or forearm be suitably oriented relative to the scanning x-ray beam 3a, e.g., with the forearm extending in the Y direction, and with the radius and ulna bones side-by-side in the X-direction. It is also desirable that the forearm and/or the wrist remain in one position during the scan, and that the positions be accurately reproducible for subsequent scans so that baseline comparisons can be made.

Referring to FIGS. 19–21, a forearm positioner 164 can be used with the scanning system described herein (as well as with pencil x-ray beam scanners). Forearm positioner 164 can be constructed of polycarbonate material, such as LEXAN, manufactured by General Electric Company, and an x-ray translucent material. It has a base portion 168 with an inboard side which faces the patient and is covered with a polyester foam layer 169 to make it more comfortable for the patient. At the outboard end of base portion 168, a ridge 170 can be constructed of a wedge-shaped piece of polyester foam which extends upwardly to aid in positioning the patient's forearm. Forearm positioner 164 has a cut-out portion 172 which is generally parallel to and proximal to and just inboard of the ridge portion 170. Forearm positioner 164 clamps over a side edge of table 50 with clamping lip portion 174. During a forearm or wrist scan data acquisition, positioner 164' is at a fixed, centrally located position on table 50. The patient sits beside table 50, with the arm over table 50 and positioner 164, and presses his or her forearm 166 down on base portion 168 and outward against ridge portion 170, as shown in more detail in FIG. 20, with the anatomical area to be scanned being over the cut-out portion 172 so that the positioner 164 would not affect the x-ray intensity measurements.

Spinal Positioning Aide

Figure 23:
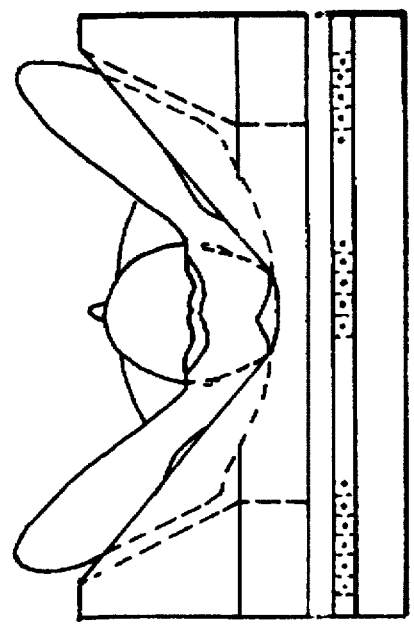
FIG. 23 is an elevational view of the positioning aide of FIG. 22, with a patient positioned thereon.
Figure 22:
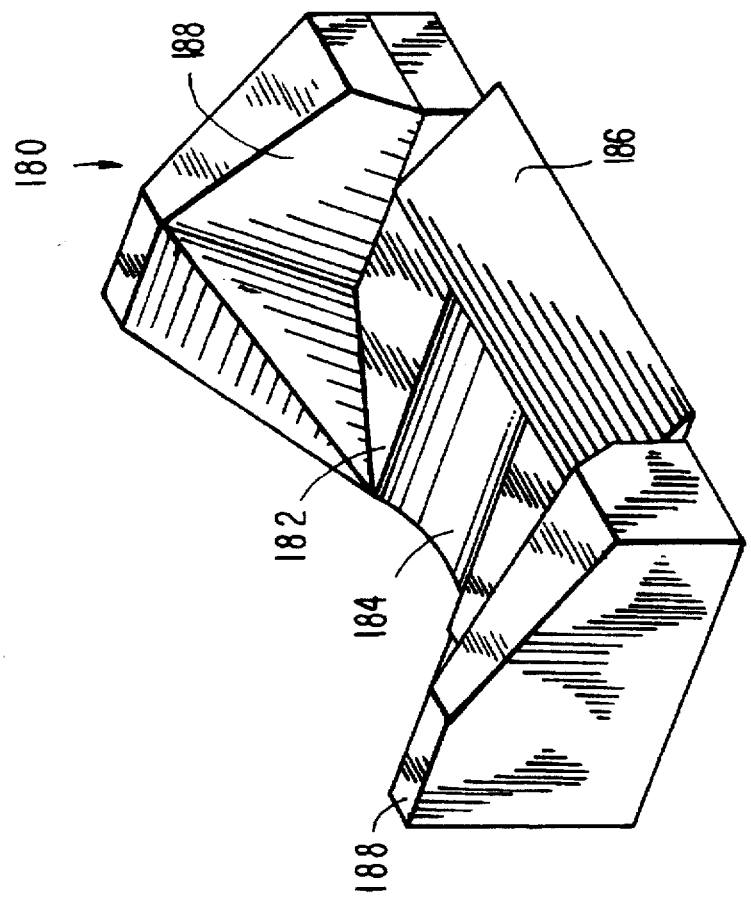
FIG. 22 is a perspective view of a spinal positioning aide of the present invention.

Referring to FIGS. 22 and 23, a spinal positioning aide 180 can be used when performing spinal scans, such as the PA and lateral scans previously described. Spinal positioner 180 is preferably constructed of x-ray translucent polyester foam and is covered with a removable material. Spinal positioner 180 helps support and position the patient's head, arms and upper shoulders in comfort and in positions which helps the spine potion which will be measured relax and extend relatively straight in the Y direction on table 50. Often, two scans are performed, one in a posterior-anterior projection and one as a lateral scan approximately ninety degrees from the first projection. The first scan obtains information which helps in carrying out the second scan. It is desirable for the accuracy of the measurement that the patient remain in the same position for both scans and that the patient's spine and hips be suitably oriented relative to scanning x-ray beam 3a.

Spinal positioner 180 has a base portion 182, with an radial indentation 184 therein which extends in the Y direction and helps support the patient's head, neck and hands. A ramped portion 186 helps support the upper shoulders and the neck. Wings 188 extend upwardly and diverge laterally away from base portion 182 to help support patient's arms such that the elbows are elevated.

For good ergonomics, spinal positioner 180 is shaped to fit the natural shape of a person who may have to remain in the position illustrated in FIG. 23 for some period of time. The angle of the ramped portion 186, which supports the patient's upper back and neck, fits the desired curvature of the spine. A drop off at the top of the ramp 186, into indentation 184, helps support the neck and head. The angular cuts in the wing portions 188 allow several different arm positions and prevent the patient's arms from rotating too far above his or her head to thereby reduce patient discomfort.

With the arms above the patient's head, as illustrated in FIG. 23, the patient's rib cage tends to rise and the scapulas tend to rotate out of their normal positions. This helps achieve a clearer projection of the upper thoracic spine region. Positioner 180 is preferably covered with a removable cover 190, seen in FIG. 23a, made of a material that is fluid proof, bacteriostatic, and removable (such as via hoop-and-loop fastening material), so it can be easily changed for a new patient.

Scanner Electrical and Electronic Control Systems

Figure 24:
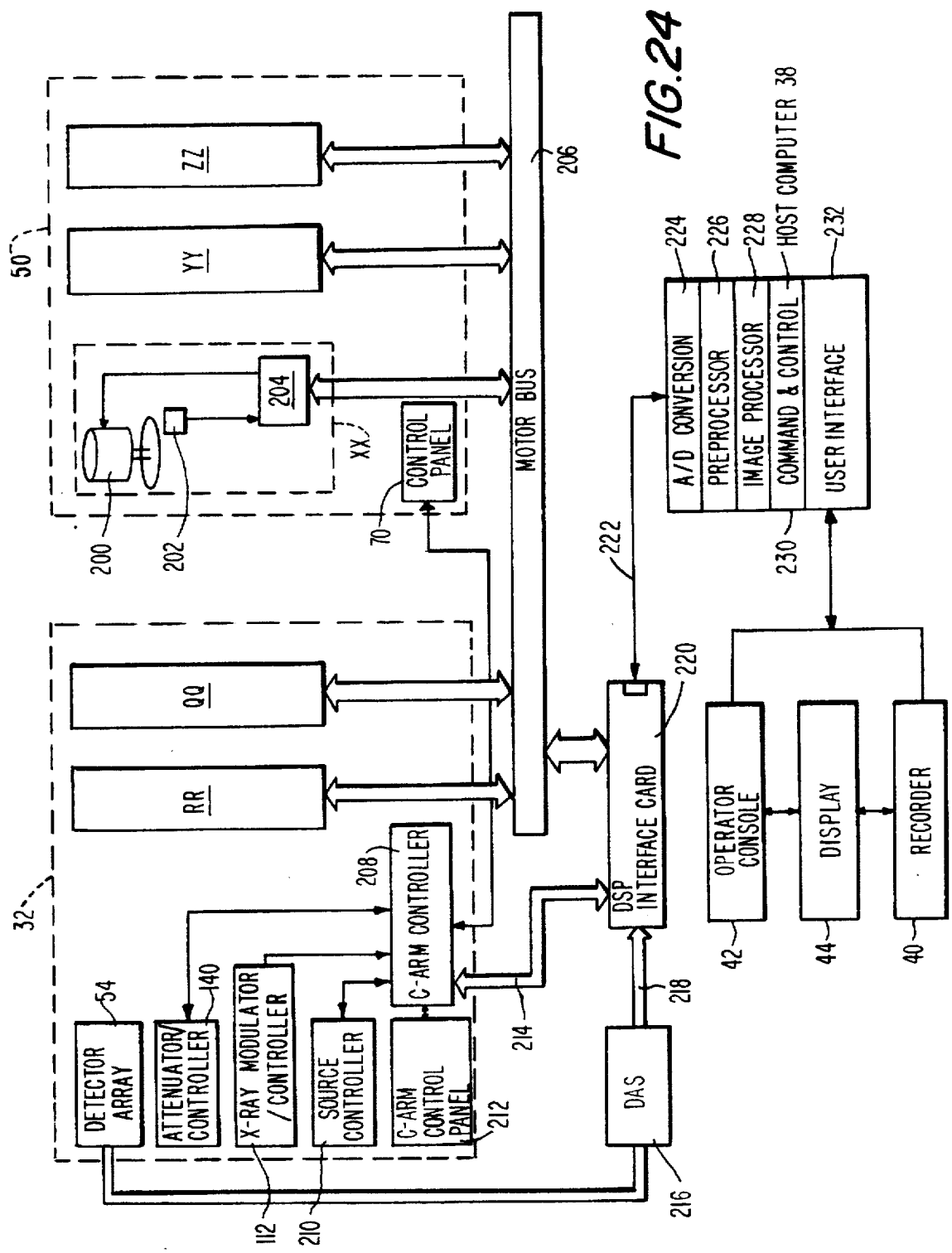
FIG. 24 is a block diagram illustrating electrical and electronic systems of an embodiment of the invention.

FIG. 24 illustrates, in block diagram form, scanner electrical and electronic control systems of an embodiment in accordance with the invention. Examination table unit 32 includes the structure illustrated in FIGS. 1 and 2, as well as a suitable power supply module 36 for x-ray source 52 and motors for driving patient support table 50 and c-arm 64, and to operate attenuator 62 and modulator 60. Each of the motors has a local controller with motor driver electronics and position encoder, similar to those used in the x-ray modulator system shown in FIG. 13. For the sake of conciseness, each of those local elements is not repeated in this figure. In FIG. 24, the drive system XX which causes X direction translation of patient table 50 is shown as including a motor 200, a motor position encoder 202 and local X motion controller/motor driver electronics 204. For the sake of brevity, similar structure for the Y direction translation of the patient table is shown as block YY, and Z direction patient table translation as block ZZ. Block RR of C-arm 56 (including c-arm 64) depicts the c-arm rotation drive system, with local controller, and block QQ denotes the c-arm translation in the Q direction (which is the same as the patient table 50 Y direction). The local controllers for drive system XX, YY, ZZ, QQ and RR communicate over motor bus 206.

As further shown in FIG. 24, the C-arm 56 has a C-arm local controller 208, which communicates with x-ray source controller 210, the x-ray modulator controller (which includes CPU 112), x-ray attenuator controller 140 and control panels (212, 70) which are located in the C-arm and patient table, respectively. C-arm controller 208 communicates via C-arm controller bus 214.

Detector array 54 supplies x-ray measurements to data acquisition system (DAS) 216, where the measurements are collected and can be preliminarily processed. DAS outputs 216 its collected and processed x-ray measurements from the individual elements of detector array 54 via DAS bus 218.

Digital Signal Processor (DSP) 220 is coupled to each of the motor bus 206, C-arm controller bus 214, and DAS bus 218, and functions as a communications exchange for the remote controllers with host computer system 38. While use of a digital signal processor 220 is shown in this embodiment, it is contemplated that any known system which can network communications between the various local processors and the host computer 38 can be used in connection with this invention. DSP 220 includes an interface for communication with the host computer in conventional fashion, such as by an ISA bus or through an industry standard interface on the card (e.g., SCSI, IEE488, etc.) to a communications line 222.

Use of distributed processing and communications networking between a plurality of local processor controllers via the DSP 220 interface, reduces wiring complexity between various controlled devices and the host computer system 38. DSP 220 is responsible for real-time processing, such as motion control over table 50 and C-arm 56. Host computer 38 also has the advantage of having a more integrated and consistent datastream content in the DSP 220 data buffers than would be communicated by all of the separate local controllers. For example, both scan data from the DAS 220 and its corresponding position data obtained from the scanning system patient table 50 and C-arm 56 position encoders (e.g., 202) can be contained in the same data buffers.

Host computer 38 provides central command and control 230 of the entire scanner system. In the embodiment shown herein, host computer 38 is an IBM AT-compatible architecture computer, having therein an 80486/25MHz or higher clock rate microcomputer, manufactured by Intel or equivalent vendor product.

In order to perform scan data processing, the ultimate goal of the scanning system, scan data from the DAS 216 is forwarded to the host computer 38, which is programmed to perform A/D conversion at 224 and preliminary data preprocessing at 226 similarly to said QDR-2000 and QDR-2000+systems. The output of the preliminary data preprocessing functions 226 is supplied to another image processing program 228, which performs various calculations and forms an image in a manner similar to that used in said earlier systems and, additionally, blends the data from successive scans (using among other things, the patient table and C-arm positional encoder data) in a manner similar to that used in second generation CT technology to form whole-body images: While the A/D conversion 224, preprocessing 226 and image processing 228 functions can be performed by the host computer 38, executing program modules, those functions can be performed in separate, dedicated data processing apparatus.

Data and images from processor program 228 are supplied to a console 42, display 44 and a recorder (e.g., floppy disk drive 40 and/or a printer) via user interface 232 for purposes and in a manner similar to those in said earlier systems. Two-way arrows connect the elements of FIG. 24 to illustrate the fact that two-way communications can take place therebetween. Conventional elements have been omitted from the Figures and from this description for the sake of conciseness.

All of the above described mechanisms are controlled and coordinated under computer control (local controller or the host computer 38). Each motion of the apparatus is monitored by an absolute encoder feedback system. All motions, except for the telescoping pedestals 68 used to raise and lower the patient table 50, employ absolute rotary encoders that do not require zero switches as would be required with incremental encoders which can only count motion from a known starting position. The use of slow speed, continuous loop belt drives for all motions except the telescoping pedestals 68, makes this technique practical. Other apparatus which employ high speed lead screw drives do not lend themselves to this simpler, absolute encoder technique because of the large number of revolutions required by the drives for positioning. Absolute encoders are restricted to a finite number of revolutions to stay within their operating range. The encoders are located and directly connected to the idler takeup pulley shaft which only rotate approximately 8 turns out of 10 allowed by the encoder during full travel for each of the various mechanisms.

The use of position encoders, such as absolute encoders, is important for monitoring and ultimately controlling the motion control systems of scanner apparatus 30. The close proximity of the structures and the potential for collisions with one another does not lend itself as well to mechanisms moving to locate zero switches to determine the location of each element of the system during power up. An important feature of absolute encoding is that location knowledge is never lost during power down/power up.

Scanner System Operation

As was previously described, x-ray source 52 is a dual-energy (DE) pulse system that is synchronized to the alternating current (AC) power source. Rotating drum cylinders 78, 80 on modulator 62 also are synchronized to the AC power line by way of modulator controller 112, which implements a closed loop control sequence. Review of the timing diagram of FIG. 14 will assist in understanding the scanning x-ray pulse sequence and modulation.

Referring to the timing diagram of FIG. 14, ACLINE represents a square wave derived from the AC line frequency (60 Hz in the United States). The term SEQUENCE describes the three energy states of the x-ray source; that is "B" for black, or no energy output pulse, "H" for the high energy emission pulse, and "L" for the low energy emission pulse. The term SEGMENT means the attenuation materials described as lining the modulator outer cylinder 80. Similarly, BRASS and AIR mean the alternating strips of brass attenuation material, and no attenuation material (i.e., "air"), along the modulator drum inner cylinder 78. SEGMENT PICKUP and INDEX signify respectively the inner 78 and outer 80 cylinder position encoders (102) output signals that are used by the controller in feedback mode to synchronize drum rotation to the AC power line frequency, and thus the x-ray source 52 energy pulsing sequence. MOTOR STEP means each step pulse command issued by the controller CPU 112 to the stepper driver electronics 113, so that the stepper motor 98 advances an additional rotational increment.

Modulator controller CPU 112 accepts commands from the host computer 38 to operate the modulator 60 in one of two modes: continuous or positioning. In the continuous mode, the stepper motor 98 for the modulator 60 is accelerated from a stopped position to a constant running speed, which is a function of the AC power frequency and the x-ray pulse mode. In the positioning mode, the stepper motor 98 is commanded to rotate until the modulator drum inner and outer cylinders are in a desired position, as determined by the modulator rotational position .encoders 102. Once the desired stationary drum position is attained, to have the needed attenuation media aligned within the x-ray beam path, the motor 98 remains energized sufficiently to prevent inadvertent drum movement, i.e., analogous to using the motor as an electromechanical brake.

When the operator starts the continuous mode of system operation, the modulator controller CPU 112 determines the AC power frequency 114 and calculates the step rate required to operate the motor 98 at a fixed number of x-ray pulses per cylinder segment. The step rate is generated from an internal timer that counts ticks of the CPU 112 clock frequency. A parabolic acceleration spiral is calculated that will "soft" start the motor 98 at a slow speed, (within the motor's starting current specifications, so as not to overload it), and accelerate it to the calculated running speed. The "soft" motor start acceleration profile is tailored to reduce the required starting torque; therefore motor size and drive system wear and tear are also minimized.

Modulator controller CPU 112 also calculates a nominal phase angle, between the AC line frequency and the modulator drum starting position indicated by the cylinder encoders 102. The modulator control system 75 then slowly steps the cylinders 78, 80 to a zero phase angle, determined by processing the encoder 102 output signals; it also sets motor power level up to a value required for smooth acceleration. Next, the CPU 112 waits for the next AC power line zero cross signal 114, then starts in ACCELERATE mode, bring the stepper motor 98 and cylinders 78, 80 up to running speed. When the motor and cylinders are at the final running speed, the CPU switches to a LOCK mode. Each time that the AC power has a zero cross, the timer that generates the step pulse frequency is reset and restarted. This reset causes the timer to discard any small variation between the crystal oscillator of the CPU and the actual AC power frequency. The stepper motor 98 can respond to small, but quick changes in the step rate, enabling synchronized cylinder and power frequency.

Where the modulator motor 98 is in synch with the AC power frequency, the phase angle between the cylinder attenuation material passage through the x-ray beam path and the x-ray generator pulse is adjusted. As the modulator cylinders rotate, the modulator controller 75 reads back the actual cylinder positions from the encoder 102 position signals and compares the delta time between the start of a new attenuation material segment and the start of an AC power line duty cycle. For a given delta time, the CPU 112 can measure the phase angle between the start of cylinder attenuation material segments and the x-ray pulses.

In order to adjust the phase angle between start of cylinder attenuation segments and the x-ray pulses to a desired value, the modulator control system 75 makes a small calculated change to the step rate timer for advancement or retardation of the phase angle. Once the phase angle is adjusted to be within programmed tolerances, the controller 75 sends a status message to the host computer 38, indicating a LOCKED condition. The CPU 112 continuously monitors the AC power frequency and the cylinder encoder 102 position signals to make timing adjustments.

The closed loop control of the pulse rate for stepper motor 98 in modulator system 60, using the AC power frequency as the reference frequency, offers advantages which include:

- relatively lower cost of stepper motors compared to larger synchronous motors utilized in prior art modulator systems;
- elimination of the need for high accuracy, expensive tachometers or encoders;
- no need for linear servo motor systems;
- the stepper motor serves a dual function as a stepper positional device when the scanning apparatus is operated in positioning mode, i.e., only one set of attenuation material layers is needed for a particular type of scan; and
- stepper electronic control systems are relatively inexpensive to implement.

Detector Calibration

The individual elements of the detector 52 are corrected for nonuniformities with angle in the fan beam and for beam hardening for different intensities. Each element of the detector 52 is also calibrated for offset and gain by taking dark level scan detector element readings which are interspersed with patient scan readings in a sampling pattern of On and Off x-ray pulses.

A. Continuous Dark Level Sampling

The system alternately turns X-rays on and off and this makes it possible to intersperse dark level measurements with x-ray signal measurements. The x-rays may be cycled on and off according to different schemes such as Off, On, Off, On ... or Off, Off, On, On, Off, Off, On, On, etc. During each On cycle, the x-ray signal is measured; during each Off cycle, the dark level offset is measured. The dark level offset can be subtracted from the time-adjacent x-ray signal measurement(s), or multiple dark level offsets can be averaged, and the average subtracted from multiple X-ray signal measurements.

An exemplary embodiment is shown in the timing diagram of FIG. 14, wherein an Off, Off, On, On, ... sequence is utilized. More particularly, the respective outputs of the x-ray detector elements in detector 54 for the two Off pulses are measured (signified by the letter "D" in the timing line SEQUENCE). Thereafter, the same measurements are taken for two pulses at a first energy level (H for "high"). Thereafter, the measurements are taken again for two Off pulses, then for two pulses at a second energy level (L for "Low"). Thereafter, two more Off pulses are measured. The sequence is repeated many times during the course of the patient scan. Twelve offset measurements are averaged to determine the dark level offset that is subtracted from each of twelve time-adjacent X-ray signal measurements. As a result of this feature of the invention, if the dark level offset varies over time, this will be accounted for correctly since the dark level offsets are measured at nearly the same time as the x-ray signals from which the offsets are subtracted. Second, a dark level offset is measured over the same time duration as the x-ray signal. Thus, the dark level offsets are measured at photon statistics corresponding to those for the x-ray signals.

B. Multiple Thickness Beam and Detector Flattening

In the preferred embodiment, variations in x-ray beam characteristics are accounted for through the use of a multiple thickness flattening system. The system utilizes the attenuator selector mechanism 62 previously described herein to take calibration readings automatically for different attenuation media under control of the host computer 38.

The flattening procedure involves collecting data representative of one or more of the modalities of which the system is capable. Reference attenuation at multiple thickness levels, and thus attenuation levels, is achieved either by means of the internal attenuator mechanism 62 or by the use of a phantom block that can be positioned between the x-ray source and detector. Data are processed by the x-ray system's computer to produce specific factors that are stored permanently for later use. Values that are stored include reference values corresponding to each attenuation level and correction factors for every detector channel at each attenuation level. Such correction factors may be calculated relative to one detector selected as the "reference", the average of more than one "reference" detector, alternative reference data, or other specified attenuation levels.

Scan acquisition software utilizes stored flattening data to make corrections to the original input data in real time as they are acquired. Alternatively, software can provides a way to store the original data and apply the flattening corrections at a later time. The exact correction for each datum point can be interpolated or extrapolated from the multiple level correction factors, based on the attenuation level relative to the reference attenuation levels. Various interpolation and extrapolation methods and algorithms can be applied to model the response of the system. Piece-wise linear interpolation and extrapolation offer the preferable characteristics of sufficient accuracy with minimal computational intensity.

C. Flattening Update

Changes in the x-ray distribution and detector gain characteristics of the system can be monitored and adjusted by means of subsequent flattening scans. Comparisons with earlier initial flattening data can provide diagnostic information and a means to make adjustments. The system can be configured to perform and analyze flattening scans on a regular, periodic basis. Moreover, a flattening scan acquired with no added attenuation, using all of the channels of detector 54, can be compared to one taken at the time of an earlier flattening procedure. Differences calculated on a respective detector element by detector element basis are applied to adjust gains in other scan modes. Thereby, drifts in gain levels can be canceled. Diagnostic information obtained through a flattening update allows for software-controlled determination of possible systematic drifts in x-ray output, changes in filtration, variations in machine geometry, or detector failure.

Limits may be set in the calibration software configuration for average drift and detector non-uniformity. If these limits are exceeded, then the operator is warned and further normal scanning may be disabled. In the case where a broken detector channel can be recognized, that channel may optionally be eliminated and replaced by interpolated values from its neighbors.

D. Exemplary Detector Calibration Calculations

In the preferred implementation, offsets of respective detector 54 element offsets can be accounted for in a linear data representation, while beam and detector flattening corrections can be applied in a logarithmic data representation.

Detector offsets are subtracted from the x-ray measurement data while in linear space. After offsets are subtracted, the data are transformed to logarithmic space for subsequent data processing and analysis. After taking the log, the attenuation at a given x-ray energy becomes linearly proportional to the x-ray thickness of a given isotropic material. In the logarithmic format, gains differences in the detector system can also be compensated through addition and subtraction. The following equation describes the data operations that are used to produce a flat image with a fan beam, multiple detector x-ray system as in the invention disclosed herein:

FLAT[detector] = log (RAW[detector] − OFFSET[detector]) +

(RAW[detector] − REF[attenuator]) * SLNUM[attenuator][detector] *

SLDEN[attenuator] + FACT[detector][attenuator] + DIFF[detector]

SLNUM[attenuator][detector] = FACT[attenuator + 1][detector] −

FACT[attenuator][detector]

SLDEN[attenuator] = (REF[attenuator + 1] − REF[attenuator])$^{-1}$ where:
[detector] is the detector channel index,
[attenuator] is the attenuator block index,
FLAT is the resulting flattened and calibrated data,
RAW is the original data (logarithmic form with offsets removed), OFFSET is the detector dark current offset,
REF is the reference attenuation array,
FACT is the array of flattening factors,
DIFF is the array of calibration differences,
SLNUM is the numerator of the slope, and
SLDEN is the denominator of the slope.

The "detector" index is applied to each detector channel in the system. The "attenuator" index is chosen such that the reference attenuation for that attenuator is the greatest that is less than the attenuation value of the original datum. Thus, there is linear interpolation when the input is between reference values and extrapolation when the attenuation value of the input exceeds the thickest attenuator.

Simultaneous Single- and Dual-Energy Imaging

Single-energy and dual-energy scans may be reconstructed from the same scan data sets and displayed simultaneously on the display monitor 44 in accordance with the invention. The scanner 30 when making dual-energy scans can store the scan sets taken at the high energy levels separately from the data taken at the low energy levels.

Spatially synchronized single-energy and dual-energy images are acquired by passing the C-arm 56 over the anatomical area of interest. The scan sets obtained at both energy levels are processed to extract densitometric information. The previously-described positional encoders in the XX, YY, ZZ, QQ and RR drive system controllers (FIG. 24) allow precise spatial registry of scan sets taken at both energy levels. The single-energy scan data can offer better spatial resolution and signal to noise characteristics than dual-energy scans. Thus, densitometric measurements as well as geometric measurements can be displayed simultaneously on the display screen 44 for evaluation by the medical practitioner.

In an alternate embodiment, three images are displayed on the same display screen (or on separate screens but at the same time so that all are available to the system user at the same time). These three images are a single energy lateral scan image of a selected region of the patient's spine, a dual energy lateral scan image of a selected region of the patient's spine, and a single energy scan or a dual energy scan taken in a posterior/anterior or an anterior posterior view. A cursor controller such as a computer mouse, trackball or sole other device allows the system user to move a cursor on one of the displayed imaged. The three images and their display controllers are registered such that any positioning or motion of the cursor on one of the images is automatically and concurrently mirrored on the other displayed images. For example, if an operator of the system manually manipulates the cursor control to place the cursor so as to mark a reference point on an edge or vertebral body LA on any one of the three images, e.g., the single energy lateral scan image, respective other cursors will automatically mark the same point on the other two images of vertebral body L4. As another example, if the operator places the cursor on the PA image to the space separating L4 and L5, the system automatically places cursor at the corresponding point between L4 and L5 on the two lateral images.

PA/Lateral Scan Measurement Processing

The separate scan lines of the PA and lateral scans can be matched spatially to enhance the diagnostic value of the information they contain. A PA scan typically is made and analyzed before performing a supine lateral scan. Once the PA scan is analyzed, the software executed by the densitometer computer system 38 can determine the center of the bone mass on each PA scan line, and then can determine an overall average center of the bone mass for the imaged portion of the spine.

In known densitometer systems, a relatively complicated computational scheme has been utilized to match spatially the PA scan lines, involving a best straight-line fit to the line-by-line bone mass centers. When performing a subsequent supine lateral scan, the table and/or the C-arm can be moved so that this center of the bone mass for the respective scan lines is positioned at a specific distance from the source.

The densitometer system of the present invention can eliminate the need to perform the best straight-line fit to the line-by-line bone mass centers. It incorporates absolute encoder positions for the patient table and C-arm positions, and the arm starting encoder position is stored with the PA scan data. Before performing the lateral scan, the starting encoder position is read from the data file, and the arm is moved to a corresponding position for the lateral scan so that the AP and lateral data are correctly aligned. This positional encoding technique allows the C-arm to be repositioned between the scans (e.g., during movement from PA to lateral scan positions) without compromising the data alignment between the PA and lateral scans.

Multiple Pass Scans For Whole Body Measurements

The method is applicable to "whole body" scans acquired by fan beam x-ray analysis apparatus 30 of the present invention as previously described. Scans that are acquired in more than one longitudinal pass along the Y direction can have the data from the separate passes combined into an image corresponding to the image that would have been obtained from a scan with a single wide x-ray beam. For a seamless reconstruction, it is desirable that the passes with the narrower angle fan beam of x-rays 3a be aligned spatially and be free of geometrical distortions. An accurate reconstruction can be accomplished if the x-ray system provides the means to orient the source, detector and subject such that there is an area of overlap between passes in which the x-ray beams are parallel and are attenuated in the same area of the subject.

A. Vertical Registration

In order to ensure accurate registration of the position of the C-arm 56 and patient support table 50 with the acquired data, an electrical position encoder is employed to provide position coordinates. In the longitudinal (Y) direction, encoder positions are acquired along with corresponding attenuation data during a scan. The encoder output is employed by the computer 38 to align the individual scan measurements after acquisition. The averaged encoder positions are used to assign a relative shifts and the data reconstruction algorithm corrects the alignment by means of data shifting and interpolation.

B. Phase Alignment

Whole body scans using multiple passes are carried out in accordance with the invention in a serpentine pattern. Time is not wasted in motions that would otherwise be needed to start each pass at the same Y position. For example, in a three pass whole body scan, the first pass scans the right side of the patient from head to toe, the second pass scans the patient's central region from toe to head, and the third pass scans the patient's left side from head to toe. The x-ray system generates multiple energy x-ray signals that are multiplexed in time, as seen in FIG. 14. An individual x-ray signal is referred to a phase, and a complete set of phases is referred to as a data line. In such a system, at a given Y position the phase in one pass can be aligned with a different phase in the neighboring pass. In order to a match the phases so that data from adjacent passes can be correctly combined into a single scan line, a new pass of data can be interpolated such that in the X-direction, a scan line from one pass would match in phase the scan line from the adjacent pass. Thus, the scan lines of the individual scan passes that are spatially aligned in the Y direction can be prepared to be combined into a single scan data line.

C. Horizontal Registration

Although c-arm 64 and table 50 positions are calculated and controlled to produce passes that are aligned in the X direction with a known amount of overlap, mechanical tolerances in the physical system can prevent perfect registration in the overlap region. In order to overcome this physical limitation and minimize artifacts at the pass boundaries, the x-ray measurement data from the overlap region is used to determine the actual amount of overlap in each scan. Adjustments are made by shifting the data points in the outer passes relative to the central pass before the passes are combined.

The actual horizontal registration is determined by examining the overlap region on each scan line. The overlap region is tested over a range of plus or minus half of the nominal overlap to find the shift that produces the maximum correlation and minimum accumulated absolute difference between the sets of attenuation data in the two passes. Empirical thresholds are applied to the correlation coefficients and difference sums to determine whether the overlap data for each scan line is reliable. The result is a sparse array of shifts for each line.

The array of shifts for each line of the outer pass is smoothed and filled or reduced to a zero or first order function to determine the exact shift for each line. If none of the data are reliable, then the nominal shift is used.

D. Scan Line Recombination

After the pass data has been registered properly, the opposing pass lines are recombined into a single data line. Data in the overlap areas are blended to minimize artifacts at the interfaces between passes. The blending is a point by point weighted average of the contributing passes, with weights that are proportional to distance of each point from the pass edge as a fraction of the overlap width.

E. Correction for Geometrical Effects

Recombined scan lines are equivalent to those that would have been acquired with a single, wide fan beam projected to a three segment detector array, with the outer segments angled downward by the angle of rotation. The effect is a compression of the image toward the scan edges. In order to correct the projection, each data line can be re-mapped, expanding the sides of the image. Correction of the distortion can produce bone density and body composition measurements that are more accurate and uniform across the scan field. An interpolation map for this purpose can be calculated to normalize the projected size of the x-ray detection face for each detector channel to the size seen by an x-ray detector element in the center pass.

While a preferred embodiment of the invention has been described in detail, it should be understood that changes and variations will be apparent to those skilled in the art which are within the scope of the invention recited in the appended claims.

Reconstructed Scan Image Processing and Manipulation

Scan data files include scan readings and accompanying positional information obtained from the outputs of the patient support table 50 and C-arm 56 position encoders (e.g., table XX translation system encoder 202). Correlation of positional information with scan information is helpful for image processing and manipulation.

A reconstructed whole-body image, or selected portion thereof, are displayed on the monitor 44, and image processing software executed by the host computer 38 is used to analyze bone mineral mass and density, bone surface area, and soft tissue composition including fat mass, lean mass and total mass.

User defined regions of interest (ROIs) can be placed in the image manually, for example by use of a mouse of the host computer 38 (not shown), or automatically by the image processing software. Exemplary ROIs such as the spine, the proximal femur, the entire femur, the tibia, the head, the calcaneus, the hand, the foot and other bony structures, can be analyzed for bone mineral mass, bone surface area, and bone density. In addition, the patient's global bone mineral content, bone surface area, and bone density can be obtained from the analysis of the entire whole-body scan image file.

Regional and global body composition analysis can also be performed on the same image file by generating, either manually or automatically, the desired ROIs within the image file. These ROIs yield information on the fat mass, lean mass and total mass of various body parts and regions including the arms, legs, trunk, viscera, pelvis, thigh, chest, head and other regions.

Advantageously, a single image file can be created for a patient, which contains one or more clinically relevant anatomical regions. Regions of interest are generated either automatically or manually by the system software. Results of the various ROI analyses are stored with the image file, providing a convenient format whereby a single, automatic measurement of a selected region contains the raw x-ray and processed data, including the measured bone mineral mass, bone mineral surface area, bone density and body composition data of one or more selected and clinically relevant anatomical sites.

Lateral projection whole-body scans can be performed for determining distribution of body fat in a patient. Such information may predict which subjects are at increased risk for various forms of cardiovascular disease and cancer. The body fat distribution calculation is performed by taking a standard PA whole body measurement, utilizing the scanner described in this specification. The source 52 and detector 54 are then rotated ninety degrees with the c-arm 64 and a lateral whole-body image is taken in a direction orthogonal to the AP scan. The AP and lateral images are then processed to determine the distribution of fat mass, lean mass and total soft tissue mass within specific regions of the body, including the pelvis, viscera, chest, upper thighs, arms and other regions.

If scan sets are taken at multiple angles, tomographic images can be reconstructed in the manner known for CT scanning. The sets can be acquired by continuously rotating the source-detector support around the patient, in the manner known for third generation CT scanners, or by moving table 50 in the X direction while the source-detector support is stationary to thereby achieve motion of fan beam 2a equivalent to that in second generation CT scanners, followed by a step rotation of the source-detector support by the angle of beam 3a minus an overlap angle, followed by another motion of table 50 in the X direction, etc., still in the manner known for second generation CT scanners.

CT Scanner Images From Bone Densitometry Scans

The system described above can generate tomographic images by collecting either single or dual energy x-ray data while C-arm 56 rotates continuously or in steps while C-arm 56 and table 50 maintain a fixed relative position along the Y-axis. In this manner, a single energy or a dual energy CT image can be obtained and can be and analyzed for bone density on the same system that acquires AP and lateral bone density data, and dual energy can be used to acquire CT data with a fan beam that is wide enough to encompass the spine but insufficiently wide to encompass the entire abdomen. This limited x-ray swath approach can be used to form an image of the bone only, and can be used for bone density measurement of the spine. The resulting CT image reconstructs the bone structure, but without showing soft tissue in the image, provided that all of bone in the slice (the spine) is encompassed in the limited width fan beam for all angles measured. Continuous or step-wise rotation of C-arm 56 is accomplished while x-ray data is being collected. Rotation through an angle greater than 180° would generally be desirable for forming a CT image using well known image reconstruction mathematics. The system described here can allow a rotation through an angle of 100°, but alternatively can be arranged to allow rotation through 180° or even more. In the alternative, the system can acquire x-ray data while C-arm 56 rotates through an angle of about 90°. The missing rays between 90° and 180° can be estimated by assuming they were equal to their corresponding rays in the range of 0° to 90°. In this approach, the spine is assumed to have bilateral symmetry so that an x-ray measurement along a ray at 10°. Whether the full complement of rays between 0° and 180° are measured or the half-complement between 0° and 90° are measured and the remaining half computed by symmetry, it is possible to acquire a series of measurements to reconstruct a CT image as is known in the art using a number of techniques such as filtered backprojection or algebraic reconstruction. A desirable different technique is to reconstruct only the bone structure for lumbar vertebrae of the spine by using the dual-energy x-ray measurements. Consider the x-ray measurements as consisting of groups of parallel rays called projections. The set of measurement can then be described as a group of projections taken at different angles. The projections can be grouped according to their being composed of either rays of high energy x-ray measurement or rays of low energy x-ray measurement. In a conventional CT scanner, a given projection in general will contain rays that extend from one side of the patient to the other. But because the fan angle of the x-ray source in the preferred embodiment of the system described here does not encompass the entire abdomen of the patient, the rays will not extend all the way to the sides of the patient. In order to reconstruct the bone structure with this limited fan angle system, the following technique is used. For each projection the quantity Q=log H-k log L is formed, where k is a number equal to the ratio of the attenuation coefficient of non-bone tissue at the low and high energies respectively. The quantity Q is related to the bone density in the projection (H is the logarithm of the high energy x-ray attenuation and L the logarithm of this low energy x-ray attenuation). When plotted in arbitrary unit of Q vs. distance across the patient along the X-direction, the general shape of the plot (in the X-direction) is a relatively flat line corresponding to tissue on one side of the spine (e.g., the left side) then a hump corresponding to the spine, then another relatively flat line for the tissue to the right of the spine, at approximately the same Q level as for the tissue on the left side. The soft tissue baseline may be set to zero for each projection. The resulting "zeroed" baseline projections can then be used to form a CT image of the bone structure alone using conventional CT reconstruction algorithm. (The "zeroed" projections correspond to x-ray dam that would be needed to form a single energy CT image of the spine embedded in the air instead of tissue). In this technique, the disclosed system collects dual energy x-ray projections over a limited view of the body which includes all of the bone in a slice but not all of the soft tissue, processes the dual energy x-ray measurements so that essentially soft tissue is cancelled, and forms a CT image which reconstructs the bone structure but not the soft tissue in a slice.

What is claimed is:

1. A medical radiological apparatus comprising:
    a patient table having a length extending along a Y-axis and a width extending along an X-axis;
    an x-ray source on one side of the patient table;
    an x-ray detector on an opposite side of the table and aligned with the x-ray source along a source-detector axis;
    the source, when selectively energized, emitting a beam of x-rays which conforms to a beam plane which is transverse to both the X-axis and the Y-axis, to scan selectively selected regions of a patient on the table with the beam of x-rays; and
    a spinal positioning aide, operative in conjunction with the patient table, including:
        a spinal base portion for selective placement on the patient table, having a radial indentation therein for retention of a patient's neck and hands; and
        a pair of wings diverging upwardly and laterally away from the spinal base portion, for supported placement of the patient's arms thereagainst, so that the patient's elbows may be elevated from, and to the left and right of the patient's torso in supported fashion.

2. A spinal positioning aide for use in conjunction with a medical radiological apparatus having a patient table, comprising:
    a spinal base portion for selective placement on a radiological apparatus patient table, having a radial indentation therein for retention of a patient's neck and hands; and a pair of wings diverging upwardly and laterally away from the spinal base portion, for supported placement of the patient's arms thereagainst, so that the patient's elbows may be elevated from, and to the left and right of the patient's torso in supported fashion.

3. The spinal positioning aide of claim 2, wherein spinal base portion is profiled to fit natural shape of a patient's spine, and wherein the spinal positioning aide further comprises a ramp portion proximal the radial indentation having a surface profile for support of the patient's neck.

4. The spinal positioning aide of claim 2, wherein the wings have angular cuts formed therein to accommodate patient varying elbow elevation.

5. The spinal positioning aide of claim 2, further comprising a removable cover.

* * * * *